US012715912B2

(12) United States Patent
Lu et al.

(10) Patent No.: US 12,715,912 B2
(45) Date of Patent: Aug. 25, 2026

(54) ANGIOPOIETIN 2, VEGF DUAL ANTAGONISTS

(71) Applicant: AskGene Pharma Inc., Camarillo, CA (US)

(72) Inventors: Yuefeng Lu, Newbury Park, CA (US); Jian-Feng Lu, Oak Park, CA (US)

(73) Assignee: AskGene Pharma Inc., Camarillo, CA (US)

( * ) Notice: Subject to any disclaimer, the term of this patent is extended or adjusted under 35 U.S.C. 154(b) by 0 days.

(21) Appl. No.: 18/460,677

(22) Filed: Sep. 4, 2023

(65) Prior Publication Data

US 2024/0101655 A1 Mar. 28, 2024

Related U.S. Application Data

(62) Division of application No. 16/741,686, filed on Jan. 13, 2020, now Pat. No. 11,746,147, which is a division of application No. 15/593,280, filed on May 11, 2017, now Pat. No. 10,654,922.

(60) Provisional application No. 62/459,046, filed on Feb. 14, 2017, provisional application No. 62/448,998, filed on Jan. 21, 2017, provisional application No. 62/336,522, filed on May 13, 2016.

(51) Int. Cl.

*C07K 16/22* (2006.01)
*A61K 39/00* (2006.01)
*C07K 14/515* (2006.01)
*C07K 14/71* (2006.01)

(52) U.S. Cl.

CPC ............ *C07K 16/22* (2013.01); *C07K 14/515* (2013.01); *C07K 14/71* (2013.01); *A61K 2039/505* (2013.01); *C07K 2317/14* (2013.01); *C07K 2317/51* (2013.01); *C07K 2317/515* (2013.01); *C07K 2317/76* (2013.01); *C07K 2317/92* (2013.01); *C07K 2319/30* (2013.01); *C07K 2319/32* (2013.01); *C07K 2319/70* (2013.01)

(58) Field of Classification Search

None

See application file for complete search history.

(56) References Cited

U.S. PATENT DOCUMENTS 7,138,370 B2 * 11/2006 Oliner ....................... A61P 9/10 514/21.4
7,608,429 B2 10/2009 Reilly et al.
8,143,380 B2 3/2012 Walker et al.
8,574,577 B2 11/2013 Barbas
9,045,545 B1 * 6/2015 Clube .................. C12Q 1/6883
10,654,922 B2 * 5/2020 Lu .......................... C07K 14/71
11,059,885 B2 * 7/2021 Lu .......................... C07K 16/22
11,746,147 B2 * 9/2023 Lu ........................ C07K 14/515 424/134.1
12,043,662 B2 * 7/2024 Lu .......................... C07K 16/22
2011/0158978 A1 6/2011 Kirchner et al.
2012/0100166 A1 4/2012 Roschke et al.
2015/0210765 A1 7/2015 Roschke et al.
2015/0216795 A1 8/2015 Assadourian et al.
2016/0017056 A1 1/2016 Clube
2016/0143852 A1 5/2016 Callahan et al.
2017/0327569 A1 11/2017 Lu et al.
2025/0188160 A1 6/2025 Lu et al.

FOREIGN PATENT DOCUMENTS

CN 109310756 A 2/2019
WO 2004/092215 A2 10/2004
WO 2005/011734 A2 2/2005
WO 2006/010057 A2 1/2006
WO 2009/058812 A1 5/2009
WO 2009/136352 A1 11/2009

OTHER PUBLICATIONS

Rudikoff et al., Proc Natl Acad Sci USA vol. 79 p. 1979 (Year: 1982).*
Lazar et al., Molecular and Cellular Biology, vol. 8, pp. 1247-1252 (Year: 1988).*
Piche-Nicholas et al., MABS 10(1): 81-94 (Year: 2018).*
Biel et al., Targeting the Angiopoietin-2/Tie-2 axis in conjunction with VEGF signal interference. Cancer Lett. Oct. 1, 2016;380(2):525-533.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Colman, Effects of amino acid sequence changes on antibody-antigen interactions. Res Immunol. Jan. 1994;145(1):33-6.
Doppalapudi et al., Chemical generation of bispecific antibodies. Proc Natl Acad Sci U S A. Dec. 28, 2010;107(52):22611-6.
Kanakaraj et al., Simultaneous targeting of TNF and Ang2 with a novel bispecific antibody enhances efficacy in an in vivo model of arthritis. MAbs. Sep.-Oct. 2012;4(5):600-13.
Kloepper et al., Ang-2/VEGF bispecific antibody reprograms macrophages and resident microglia to anti-tumor phenotype and prolongs glioblastoma survival. Proc Natl Acad Sci U S A. Apr. 19, 2016;113(16):4476-81.
Lloyd et al., Modelling the human immune response: performance of a 1011 human antibody repertoire against a broad panel of therapeutically relevant antigens. Progein Engineering Design & Selection. 2009;22(3):159-168.

(Continued)

*Primary Examiner* — Phuong Huynh

(74) *Attorney, Agent, or Firm* — McCarter & English, LLP; Yu Lu

(57) ABSTRACT

The present disclosure relates to chimeric molecules which are fusion proteins comprising two components: an Ang-2 binding peptide linked to either a VEGF antibody or a VEGF receptor-Fc fusion protein. The Ang2 peptide, VEGF antibody, and VEGF receptor-Fc fusion proteins are each defined below with reference to percent identity to a reference sequence. The chimeric molecule is a fusion protein, dual antagonist of Ang2 and VEGF for treatment of cancers, proliferative retinopathies, neovascular glaucoma, macular edema, AMD, and rheumatoid arthritis.

6 Claims, 5 Drawing Sheets

Specification includes a Sequence Listing.

(56) References Cited

OTHER PUBLICATIONS

Presta et al., Humanization of an anti-vascular endothelial growth factor monoclonal antibody for the therapy of solid tumors and other disorders. Cancer Res. Oct. 15, 1997;57(20):4593-9.
Skolnick et al., From genes to protein structure and function: novel applications of computational approaches in the genomic era. Trends Biotechnol. Jan. 2000;18(1):34-9.
Wu et al., Humanization of a murine monoclonal antibody by simultaneous optimization of framework and CDR residues. J Mol Biol. Nov. 19, 1999;294(1):151-62.
Yu et al., Interaction between bevacizumab and murine VEGF-A: a reassessment. Invest Ophthalmol Vis Sci. Feb. 2008;49(2):522-7.
European Office Action for Application No. 17796892.2, dated Jul. 20, 2020, 14 pages.
International Search Report and Written Opinion for Application No. PCT/US2017/032289, dated Oct. 6, 2017, 13 pages.
International Search Report and Written Opinion for Application No. PCT/US2019/026838, dated Jul. 15, 2019, 4 pages.

* cited by examiner

ANGIOPOIETIN 2, VEGF DUAL ANTAGONISTS

CROSS-REFERENCE TO RELATED APPLICATIONS

The present application is a divisional application of U.S. application Ser. No. 16/741,686, filed Jan. 13, 2020, now U.S. Pat. No. 11,746,147, which issued Sep. 5, 2023, which is a divisional application of U.S. application Ser. No. 15/593,280, filed May 11, 2017, now U.S. Pat. No. 10,654,922, which issued May 19, 2020. U.S. application Ser. No. 15/593,280 claims priority to U.S. Provisional Patent Application No. 62/336,522, filed May 13, 2016,U.S. Provisional Patent Application No. 62/448,998, filed Jan. 21, 2017, and U.S. Provisional Patent Application No. 62/459,046, filed Feb. 14, 2017, each of which is incorporated herein by reference in their entirety.

REFERENCE TO SEQUENCE LISTING

The entire content of the following electronic submission of the sequence listing via the USPTO EFS-WEB server, as authorized and set forth in MPEP § 1730II.B.2(a)(C), is hereby expressly incorporated by reference in its entirety for all purposes. The sequence listing is identified on the electronically filed text file as follows: File Name: AG3-006USD2; Date of Creation: Oct. 12, 2023;Size (bytes): 45 KB.

INTRODUCTION

Angiogenesis is implicated in the pathogenesis of a variety of disorders including solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al, Annu. Rev. Physiol. 53 (1991) 217-239; and Garner, A., Vascular Diseases, in: Pathobiology of Ocular Disease, A Dynamic Approach, Garner, A., and Klintworth, G. K. (eds.), 2nd edition, Marcel Dekker, New York (1994), pp. 1625-1710). In the case of solid tumors, the neovascularization allows the tumor cells to acquire a growth advantage and proliferative autonomy compared to the normal cells. Accordingly, a correlation has been observed between density of microvessels in tumor sections and patient survival in a number of cancers (see, e.g., Weidner, N., et al, N Engl J Med. 324 (1991) 1-8; Horak, E. R., et al, Lancet 340 (1992) 1120-1124; and Macchiarini, P., et al, Lancet 340 (1992) 145-146).

Human vascular endothelial growth factor (VEGF/VEGF-A) is described in, e.g., Leung, D. W., et al, Science 246 (1989) 1306-9; Keck, P. J., et al, Science 246 (1989) 1309-12 and Connolly, D. T., et al, J. Biol. Chem. 264 (1989) 20017-24. The expression of VEGF is potentiated in response to hypoxia, by activated oncogenes, and by a variety of cytokines. VEGF is involved in the regulation of normal and abnormal angiogenesis and neovascularization associated with tumors and intraocular disorders (Ferrara, N., et al, Endocr. Rev. 18 (1997) 4-25; Berkman, R. A., et al, J. Clin. Invest. 91 (1993) 153-159; Brown, L. F., et al, Human Pathol. 26 (1995) 86-91; Brown, L. F., et al, Cancer Res. 53 (1993) 4727-4735; Mattern, J., et al, Brit. J. Cancer. 73 (1996) 931-934; and Dvorak, H. F., et al, Am. J. Pathol. 146 (1995) 1029-1039).

Deregulated VEGF expression contributes to the development of solid tumors by promoting tumor angiogenesis and to the etiology of several additional diseases that are characterized by abnormal angiogenesis (Kim, K. J., et al., 1993. Nature (London) 362, 841-844; Millauer, B., et al., 1994. Nature (London) 367, 576-579). Consequently, inhibition of VEGF signaling abrogates the development of a wide variety of tumors.

In retinopathies, in which partial or general ischemia of the retina is accompanied by overexpression of VEGF and hyperproliferation of blood vessels, blindness can result (Aiello, L. P et al., 1994. N. Engl. J. Med. 331, 1480-1487; Adamis, A. P., et al., Am. J. Ophthalmol. 118, 445-450). Inhibition of VEGF expression in such disease states can treat or prevent resulting blindness.

Two VEGF receptors belonging to the tyrosine-kinase receptor family have been identified and cloned: the VEGFR-1 and the VEGFR-2 receptors (Devries, C. et al., 1992. Science 255, 989-991; Terman, B. I., et al., Biochem. Biophys. Res. Commun. 187, 1579-1586; Matthews, W., et al., 1991. Cell 65, 1143-1152; Shibuya, M., et al. 1990. Oncogene 5, 519-524). These receptors form a subfamily distinguished by the presence of seven immunoglobulin-like loops in their extracellular part and a split tyrosine-kinase domain in their intracellular part. The VEGFR-2 and VEGFR-1 receptors are expressed predominantly in endothelial cells, but a few additional types of cells express one or both of these receptors.

Efforts to inhibit VEGF-induced tumor angiogenesis include the development of humanized neutralizing anti-VEGF monoclonal antibodies (see, e.g., Presta, L. G. et al., Cancer Res. 57, 4593-4599 (1997); U.S. Pat. No. 6,884,879, WO 94/10202, WO 98/45332, WO 2005/00900 and WO 00/35956), and inhibitory soluble VEGF receptors (Kendall, R. L., and Thomas, K. A. Proc. Natl. Acad. Sci. USA 90, 10705-10709; Lin, P. N., et al., 1998. Cell Growth Differ. 9, 49-58). For example, the humanized monoclonal antibody bevacizumab (sold under the trade name Avastin®) is an anti-VEGF antibody used in tumor therapy (see, e.g., WO 98/45331). Ranibizumab (trade name Lucentis®) is a monoclonal antibody fragment derived from the same parent murine antibody as bevacizumab. It is much smaller than the parent molecule and has been affinity matured to provide stronger binding to VEGF-A (WO 98/45331). It is an anti-angiogenic that has been approved to treat the "wet" type of age-related macular degeneration (ARMD), a common form of age-related vision loss. Aflibercept is a recombinant fusion protein consisting of VEGF-binding portions from the extracellular domains of human VEGF receptors 1 and 2, that are fused to the Fc portion of the human IgG1 immunoglobulin.

Human angiopoietin-2 (ANG-2) (alternatively abbreviated with ANGPT2 or ANG2) is described in Maisonpierre, P. C., et al, Science 277 (1997) 55-60 and Cheung, A. H., et al, Genomics 48 (1998) 389-91. The angiopoietins-1 and -2 and were discovered as ligands for the Ties, a family of tyrosine kinases that is selectively expressed within the vascular endothelium. Yancopoulos, G. D., et al, Nature 407 (2000) 242-48. Ang-1 was shown to support EC survival and to promote endothelium integrity, Davis, S., et al, Cell 87 (1996) 1161-69; Kwak, H. J., et al, FEBS Lett 448 (1999) 249-53; Suri, C, et al, Science 282 (1998) 468-71; Thurston, G., et al, Science 286 (1999) 2511-2514; Thurston, G., et al, Nat. Med. 6 (2000) 460-63, whereas ANG-2 had the opposite effect and promoted blood vessel destabilization and regression in the absence of the survival factors VEGF or basic fibroblast growth factor. Maisonpierre, P. C., et al, Science 277 (1997) 55-60. However, many studies of ANG-2 function have suggested a more complex situation.

ANG-2 might be a complex regulator of vascular remodeling that plays a role in both vessel sprouting and vessel regression.

In adult individuals, ANG-2 expression is restricted to sites of vascular remodeling as well as in highly vascularized tumors, including glioma, Osada, H., et al, Int. J. Oncol. 18 (2001) 305-09); Koga, K., et al, Cancer Res. 61 (2001) 6248-54, hepatocellular carcinoma, Tanaka, S., et al., J. Clin. Invest. 103 (1999) 341-45, gastric carcinoma, Etoh, T., et al, Cancer Res. 61 (2001) 2145-53; Lee, J. H., et al, Int. J. Oncol. 18 (2001) 355-61, thyroid tumor, Bunone, G., et al, Am J Pathol 155 (1999) 1967-76 non-small cell lung cancer, Wong, M. P., et al, Lung Cancer 29 (2000) 11-22, cancer of colon, Ahmad, S. A., et al, Cancer 92 (2001) 1138-43, and prostate cancer Wurmbach, J. H., et al., Anticancer Res. 20 (2000) 5217-20. By detecting ANG-2 niRNA levels in archived human breast cancer specimens, Sfiligoi, C, et al, Int. J. Cancer 103 (2003) 466-74 reported that ANG-2 mRNA is significantly associated with auxiliary lymph node invasion, short disease-free time and poor overall survival. Tanaka, F., et al., Cancer Res. 62 (2002) 7124-29 reviewed a total of 236 patients of non-small cell lung cancer (NSCLC) with pathological stage-I to -IIIA, respectively. Using immunohistochemistry, they found that 16.9% of the NSCLC patients were ANG-2 positive. The microvessel density for ANG-2 positive tumor is significantly higher than that of ANG-2 negative. Such an angiogenic effect of ANG-2 was seen only when VEGF expression was high. Moreover, positive expression of ANG-2 was a significant factor to predict a poor postoperative survival. Tanaka, F., et al, Cancer Res. 62 (2002) 7124-7129. These results suggest that ANG-2 is an indicator of poor prognosis patients with several types of cancer.

In recent years Angiopoietin-1, Angiopoietin-2 and/or Tie-2 have been proposed as possible anti-cancer therapeutic targets. For example, U.S. Pat. Nos. 6,166,185, 5,650,490 and 5,814,464 each disclose anti-Tie-2 ligand and receptor antibodies. Effective anti-Angiopoietin-2 therapy is thought to be of benefit in treating diseases such as cancer, in which progression is dependent on aberrant angiogenesis where blocking the process can lead to prevention of disease advancement (Folkman, J., Nature Medicine. 1 (1995) 27-31). In addition, some groups have reported the use of antibodies and peptides that bind to Angiopoietin-2, such as the peptides 2×Con4(C), L1-7, L1-10, and L1-15, as described in WO2004/092215 and WO2003/05134, and block the interaction between Angiopoietin-2 and Tie-2. According to WO2003/05134, 2×Con4(C) also bound to Angiopoietin-1 and inhibited its interaction with Tie-2, while peptides L1-7, L-10 and L1-15 had little affinity for Angiopoietin-1. For additional Ang2 binding peptides, see, for example, U.S. Pat. Nos. 6,166,185, 7,666,832, US 2003/10124129. WO 03/030833, WO 2006/068953, WO 03/057134 or US 2006/0122370.

A wide variety of recombinant antibody formats have been developed in the recent past, e.g., tetravalent bispecific antibodies by fusion of, e.g., an IgG antibody format and single chain domains (see e.g., Coloma, M. J., et al, Nature Biotech 15 (1997) 159-163; WO 2001/077342; and Morrison, S. L., Nature Biotech 25 (2007) 1233-1234).

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al, Nature Biotech 23 (2005) 1126-1136; Fischer, N., Leger, O., Pathobiology 74 (2007) 3-14; Shen, J., et al, Journal of Immunological Methods 318 (2007) 65-74; Wu, C, et al, Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer, N., Leger, O., Pathobiology 74 (2007) 3-14). It has to be kept in mind that one may want to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring antibodies.

In WO 2007/024715 are reported dual variable domain immunoglobulins as engineered multivalent and multispecific binding proteins. A process for the preparation of biologically active antibody dimers is reported in U.S. Pat. No. 6,897,044. Multivalent Fv antibody construct having at least four variable domains which are linked with each over via peptide linkers are reported in U.S. Pat. No. 7,129,330. Dimeric and multimeric antigen binding structures are reported in US 2005/0079170. Tri- or tetra-valent monospecific antigen-binding protein comprising three or four Fab fragments bound to each other covalently by a connecting structure, which protein is not a natural immunoglobulin are reported in U.S. Pat. No. 6,511,663. In WO 2006/020258 tetravalent bispecific antibodies are reported that can be efficiently expressed in prokaryotic and eukaryotic cells, and are useful in therapeutic and diagnostic methods. A method of separating or preferentially synthesizing dimers which are linked via at least one interchain disulfide linkage from dimers which are not linked via at least one interchain disulfide linkage from a mixture comprising the two types of polypeptide dimers is reported in US 2005/0163782. Bispecific tetravalent receptors are reported in U.S. Pat. No. 5,959,083. Engineered antibodies with three or more functional antigen binding sites are reported in WO 2001/077342.

Multispecific and multivalent antigen-binding polypeptides are reported in WO 1997/001580. WO 1992/004053 reports homoconjugates, typically prepared from monoclonal antibodies of the IgG class which bind to the same antigenic determinant are covalently linked by synthetic cross-linking. Oligomeric monoclonal antibodies with high avidity for antigen are reported in WO 1991/06305 whereby the oligomers, typically of the IgG class, are secreted having two or more immunoglobulin monomers associated together to form tetravalent or hexavalent IgG molecules. Sheep-derived antibodies and engineered antibody constructs are reported in U.S. Pat. No. 6,350,860, which can be used to treat diseases wherein interferon gamma activity is pathogenic. In US 2005/0100543 are reported targetable constructs that are multivalent carriers of bi-specific antibodies, i.e., each molecule of a targetable construct can serve as a carrier of two or more bi-specific antibodies. Genetically engineered bispecific tetravalent antibodies are reported in WO 1995/009917. In WO 2007/109254 stabilized binding molecules that consist of or comprise a stabilized scFv are reported.

Combination of VEGF and ANG-2 inhibitors in WO 2007/068895 refers to a combination of an ANG-2 antagonist and a VEGF, KDR and/or FLTL antagonist. WO 2007/089445 refers to ANG-2 and VEGF inhibitor combinations. WO 2003/106501 refers to fusion proteins binding to Angiopoietin and containing a multimerization domain. WO 2008/132568 relates to fusion proteins binding to Angiopoietin and VEGF. WO 2003/020906 relates to multivalent protein conjugates with multiple ligand-binding domains of receptors.

As opposed to the compositions described above, the present specification contemplates the use of a dual antagonist. The chimeric protein of the invention comprises an Ang2 binding peptide fused to either a VEGF antibody or a VEGF receptor-Fc fusion protein. The efficacy obtained with a dual antagonist of the present disclosure is synergistically improved in comparison to either the native protein antagonist/inhibitor or a construct directed to a single antagonist.

SUMMARY

In one aspect, the present invention provides a chimeric molecule comprising:

a. an anti-VEGF antibody or a VEGF receptor-Fc-fusion; and
b. a peptide that binds to angiopoietin 2 (Ang2);
c. wherein the peptide that binds to Ang2 comprises a sequence having at least 70%, at least 75%, at least 80%, at least 85%, at least 90%, at least 95%, at least 96%, at least 97%, at least 98%, at least 99% or 100% sequence identity to SEQ ID NO:1; and
d. wherein the chimeric molecule inhibits the binding of VEGF to a VEGF receptor and inhibits binding of Ang2 to an Ang2 receptor.

In one embodiment, the Ang2 binding peptide is fused to the C-terminus of the heavy chain of the anti-VEGF antibody, wherein the chimeric molecule also comprises a light chain.

In one embodiment, the anti-VEGF antibody comprises a heavy chain and a light chain, wherein the heavy chain comprising a sequence having at least 70%, at least 75%, at least 80%, at least 85%, at least 90%, at least 95%, at least 96%, at least 97%, at least 98%, at least 99% or 100% sequence identity to SEQ ID NO:2; and wherein the light chain comprises a sequence having at least 70%, at least 75%, at least 80%, at least 85%, at least 90%, at least 95%, at least 96%, at least 97%, at least 98%, at least 99% or 100% sequence identity to SEQ ID NO:3.

In one embodiment, the Ang2 binding peptide fused to the C-terminus of the heavy chain of the anti-VEGF antibody, wherein the chimeric molecule comprises a sequence having at least 70%, at least 75%, at least 80%, at least 85%, at least 90%, at least 95%, at least 96%, at least 97%, at least 98%, at least 99% or 100% sequence identity to SEQ ID NO:4 or SEQ ID NO:17; wherein the chimeric molecule also comprises a light chain comprises a sequence having at least 70%, at least 75%, at least 80%, at least 85%, at least 90%, at least 95%, at least 96%, at least 97%, at least 98%, at least 99% or 100% sequence identity to SEQ ID NO:3.

In one embodiment, the VEGF receptor-Fc fusion comprises a sequence having at least 70%, at least 75%, at least 80%, at least 85%, at least 90%, at least 95%, at least 96%, at least 97%, at least 98%, at least 99% or 100% sequence identity to SEQ ID NO:5.

In one embodiment, the polypeptide comprising the Ang2 binding peptide fused to the C-terminus of the VEGF-Fc fusion protein, wherein the chimeric molecule comprises a sequence having at least 70%, at least 75%, at least 80%, at least 85%, at least 90%, at least 95%, at least 96%, at least 97%, at least 98%, at least 99% or 100% sequence identity to SEQ ID NO:6.

In one embodiment, the Ang2 binding protein is fused to the C-terminus of the VEGF receptor-Fc fusion.

In one embodiment, the VEGF antibody is selected from a single-chain Fv antibody (scFv), a Fab antibody, a Fab' antibody, a (Fab')2 antibody, a domain antibody, a nanobody, a minibody, a maxibody, and a diabody.

In one aspect, the invention provides a chimeric molecule, which comprises an antibody and an Ang2 binding peptide, wherein said peptide is fused to the N-terminus or C-terminus of the light chains and/or heavy chains of said antibody, optionally with a peptide linker, wherein the peptide has an amino acid sequence with at least 80%, at least 85%, at least 90%, at least 95%, or 100% identity to a peptide selected from the group consisting of SEQ ID NOS:7-12, and wherein said antibody binds to VEGF.

In one embodiment, said antibody has a heavy chain with amino acid sequence at least 95% identity to that of SEQ ID NO:2, and light chain with amino acid sequence at least 95% identity to SEQ ID NO:3.

In one embodiment, the chimeric molecule comprises a peptide-light chain fusion with an amino acid sequence at least 98%, at least 99%, or 100% identical to SEQ ID NO 14, wherein said chimeric molecule further comprises a heavy chain with amino acid sequence at least 99% identical to that of SEQ ID NO:2.

In one embodiment, the chimeric molecule comprises a peptide-heavy chain fusion molecule with an amino acid sequence at least 98%, at least 99%, or 100% identical to SEQ ID NO 15 or SEQ ID NO 16, wherein said chimeric molecule further comprises a light chain with amino acid sequence at least 99% identical to that of SEQ ID NO:3.

In one embodiment, the chimeric molecule comprises a peptide-light chain fusion with an amino acid sequence at least 98%, at least 99%, or 100% identical to SEQ ID NO:14, wherein it further comprises a peptide-heavy chain fusion molecule with an amino acid sequence at least 98%, at least 99%, or 100% identical to SEQ ID NO:15 or SEQ ID NO:16.

In one embodiment, said peptide is fused to the N-terminal or C-terminal of said protein, optionally with a peptide linker, wherein the peptide has an amino acid sequence with at 80%, at least 85%, at least 90%, at least 95%, or 100% identity to a peptide selected from the group consisting of SEQ ID NOS:7-12, and wherein said protein has an amino acid sequence of at least 95% identity to that of SEQ ID NO:5.

In one embodiment, the fusion molecule forms a homologous dimer, and wherein the dimer binds to both VEGF and Ang 2.

In one aspect, the invention provides polynucleotides encoding the chimeric molecules described above, an expression vector comprising the polynucleotide, a host cell transfected with the vector, and a method of producing a chimeric molecule comprising culturing the host cell.

In one aspect the invention provides a pharmaceutical composition comprising a chimeric molecules and a pharmaceutically acceptable carrier.

In one aspect, the invention provides a method of treating cancer, proliferative retinopathy, age-related macular degeneration or rheumatoid arthritis comprising administering to a subject a pharmaceutical composition as described above.

In one embodiment, the cancer is selected from the group consisting of colon, lung, breast, renal and brain cancer.

DETAILED DESCRIPTION OF THE INVENTION

Figure 1:
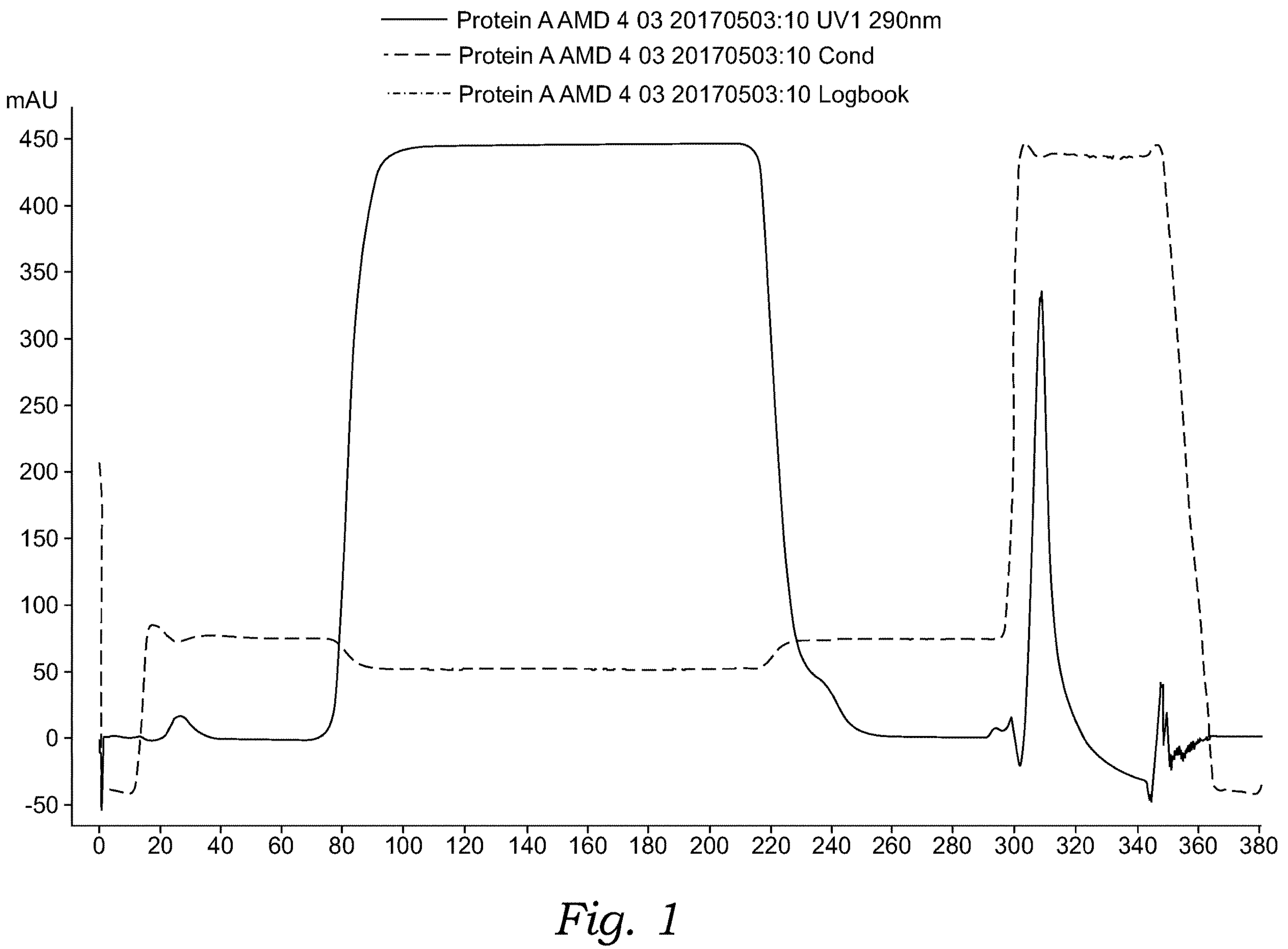
FIG. 1. Protein A Affinity Chromatography. Approximately 150 ml of the clarified HEK 293 cell culture medium of the transient expression of AMD-B was loaded to a Protein A column (1×17 cm (Diameter×Height) of Captiv A Protein A resin) at 3 ml/min. The protein A column was equilibrated with an equilibration buffer (25 mM Tris Buffer, 100 mM NaCl, PH approximately 7.2). The column was washed with the Equilibration buffer and eluted with 2 M ariginine solution, PH 4.

Disclosed herein are chimeric proteins which are fusion proteins comprising two components: an Ang-2 binding peptide linked to either a VEGF antibody or a VEGF receptor-Fc fusion protein. The Ang2 peptide, VEGF antibody, and VEGF receptor-Fc fusion proteins are each defined below with reference to percent identity to a reference sequence. The chimeric protein is a fusion protein, dual antagonist of Ang2 and VEGF for treatment of cancers, proliferative retinopathies, neovascular glaucoma, macular edema, AMD, and rheumatoid arthritis.

The chimeric protein comprises a Ang2 peptide component, which binds to Angiopoietin 2 (Ang2) and inhibits the binding of Ang2 to its receptor. One example of the peptide is called 2×Con4(C), as described in WO2004/092215A2 or WO03/05134A2. 2×Con4(C) has an amino acid sequence as shown in SEQ ID NO:1. Additional examples of Ang2 binding peptides include but are not limited to: L1-7, L1-10, and L1-15, as described in WO2004/092215A2. Those peptides have amino acid sequences as shown in SEQ ID NO: 7-9.

The chimeric protein comprises one of two additional components. The first of the additional components is a VEGF antibody that inhibits the binding of VEGF to its receptors. One example of the VEGF antibody is bevacizumab, which has two heavy chains with amino acid sequence as shown as SEQ ID NO:2, and two light chains with amino acid sequence as shown as SEQ ID NO:3.

The second of the additional components is a VEGF receptor-Fc fusion protein which "traps" VEGF and competes with the naturally occurring VEGF cellular receptor to inhibit VEGF. One example of the VEGF-receptor Fc fusion protein is afilbercept, which has an amino acid sequence as shown in SEQ ID NO:5.

The fusion proteins can be made entirely through recombinant expression with or without amino acid linkers between the components of the chimeric protein; alternatively, they can be made with or without linkers through protein native chemical ligation (NCL) or site specific conjugation, wherein the peptide is chemically synthesized and the VEGF antibody or the VEGF receptor-Fc fusion protein molecules are recombinant expressed.

The Ang2 peptide can be linked or fused to either the C- or N-terminus of the VEGF antibody (e.g., either the heavy or the light chains) or the VEGF receptor-Fc fusion protein. The Fc portion of the VEGF receptor-Fc fusion protein may be located at either the C- or N-terminus of the VEGF receptor protein. The Fc portion is further defined herein.

The resulting molecules possess dual-antagonist activities and have therapeutic effects for cancers, proliferative retinopathies, diabetic retinopathies, age-related macular degeneration and rheumatoid arthritis.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing, isolating, purifying, synthesizing, and recombinantly manufacturing) polypeptides are well known to one of ordinary skill in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The present composition encompasses amino acid substitutions in proteins and peptides, which do not generally alter the activity of the proteins or peptides (H. Neurath, R. L. Hill, The Proteins, Academic Press, New York, 1979). In one embodiment, these substitutions are "conservative" amino acid substitutions. The most commonly occurring substitutions are Ala/Ser, Val/Ile, Asp/Glu, Thr/Ser, Ala/Gly, Ala/Thr, Ser/Asn, Ala/Val, Ser/Gly, Ala/Pro, Lys/Arg, Asp/Asn, Leu/Ile, Leu/Val, Ala/Glu and Asp/Gly, in both directions As to "conservatively modified variants" of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Analogue as used herein denotes a peptide, polypeptide, or protein sequence which differs from a reference peptide, polypeptide, or protein sequence. Such differences may be the addition, deletion, or substitution of amino acids, phosphorylation, sulfation, acrylation, glycosylation, methylation, farnesylation, acetylation, amidation, and the like, the use of non-natural amino acid structures, or other such modifications as known in the art.

The term "unnatural amino acids" as used herein refers to amino acids other than the 20 typical amino acids found in the proteins in our human body. Unnatural amino acids are non-proteinogenic amino acids that either occur naturally or are chemically synthesized. They may include but are not limited to aminoisobutyric acid (Aib), β-amino acids ($\beta^3$ and $\beta^2$), homo-amino acids, Proline and Pyruvic acid derivatives, 3-substituted Alanine derivatives. Glycine derivatives, Ring-substituted Phenylalanine and Tyrosine derivatives, Linear core amino acids, diamino acids, D-amino acids and N-methyl amino acids.

Further an N-terminal amino acid may be modified by coupling an imidazolic group to the N-terminal amino acid of a polypeptide. Such imidazolic groups can be 4-imidazopropionyl (des-amino-histidyl), 4-amidzoacetyl, 5-imidazo-α, α dimethyl-acetyl. Coupling the imidazolic group to the present fusion peptide or portions thereof may be accomplished by synthetic chemical means. Because many of the various organic groups comtemplated herein contain a carboxylic acid, the imidazolic group can be added by solid phase protein synthesis analogous to adding an amino acid to the N-terminus of a polypeptide. Alternatively, an activated ester of the imidazolic groups may be denoted by "CA-" appearing prior to the N-terminal of a peptide or protein. In one embodiment, the imidazolic group is a 4-imidzoacetyl group.

An Ang2 peptide of the invention is a peptide that binds to Ang2 protein and comprises a sequence having at least 70%, at least 75%, at least 80%, at least 85%, at least 90%, at least 95%, at least 96%, at least 97%, at least 98%, at least 99% or 100% sequence identity to SEQ ID NO:1.

The anti-VEGF antibody of the invention may comprise a heavy chain and a light chain, wherein the heavy chain comprising a sequence having at least 70%, at least 75%, at least 80%, at least 85%, at least 90%, at least 95%, at least 96%, at least 97%, at least 98%, at least 99% or 100% sequence identity to SEQ ID NO:2; and wherein the light chain comprises a sequence having at least 70%, at least 75%, at least 80%, at least 85%, at least 90%, at least 95%, at least 96%, at least 97%, at least 98%, at least 99% or 100% sequence identity to SEQ ID NO:3.

A VEGF receptor-Fc fusion protein of the invention is a sequence having at least 70%, at least 75%, at least 80%, at least 85%, at least 90%, at least 95%, at least 96%, at least 97%, at least 98%, at least 99% or 100% sequence identity to SEQ ID NO:5.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (V.sub.L) and variable heavy chain (V.sub.H) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'.sub.2, a dimer of Fab which itself is a light chain joined to V.sub.H-C.sub.H1 by a disulfide bond. The F(ab)'.sub.2 may be reduced under mild conditions to break the disulfide linkage in the hinge region, thereby converting the F(ab)'.sub.2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

Accordingly, in either aspect of the invention, the term antibody also embraces minibodies, diabodies, triabodies and the like. Diabodies are small bivalent biospecific antibody fragments with high avidity and specificity. Their high signal to noise ratio is typically better due to a better specificity and fast blood clearance increasing their potential for diagnostic and therapeutic targeting of specific antigen (Sundaresan et al., J Nucl Med 44:1962-9 (2003). In addition, these antibodies are advantageous because they can be engineered if necessary as different types of antibody fragments ranging from a small single chain Fv to an intact IgG with varying isoforms (Wu & Senter, Nat. Biotechnol. 23:1137-1146 (2005)). In some embodiments, the antibody fragment is part of a diabody. In some embodiments, in either aspect, the invention provides high avidity antibodies for use according to the invention.

In some embodiments, the present invention provides anti-VEGF sequences comprising CDR regions of SEQ ID NOS: 2 and 3 or a sequence having at least 70%, at least 75%, at least 80%, at least 85%, at least 90%, at least 95%, at least 96%, at least 97%, at least 98%, at least 99% or 100% sequence identity to SEQ ID NO:2 or 3. The CDR regions provided by the invention may be used to construct an anti-VEGF binding protein, including without limitation, an antibody, a scFv, a triabody, a diabody, a minibody, and the like. In a certain embodiment, an anti-VEGF binding protein of the invention will comprise at least one CDR region from SEQ ID NOS: 2 or 3 or a sequence having at least 70%, at least 75%, at least 80%, at least 85%, at least 90%, at least 95%, at least 96%, at least 97%, at least 98%, at least 99% or 100% sequence identity to SEQ ID NOS: 2 or 3. Anti-VEGF binding proteins may comprise, for example, a CDR-H1, a CDR-H2, a CDR-H3, a CDR-L1, a CDR-L2, a CDR-L3, or combinations thereof, from an antibody provided herein. In particular embodiments of the invention, an anti-VEGF binding protein may comprise all three CDR-H sequences of an antibody provided herein, all three CDR-L sequences of an antibody provided herein, or both. Anti-VEGF CDR sequences may be used on an antibody backbone, or fragment thereof, and likewise may include humanized antibodies, or antibodies containing humanized sequences. In some embodiments, the CDR regions may be defined using the Kabat definition, the Chothia definition, the AbM definition, the contact definition, or any other suitable CDR numbering system.

In some embodiments, the invention provides antibodies (e.g., diabodies, minibodies, triabodies) or fragments thereof having the CDRs of SEQ ID NOS: 2 or 3 or a sequence having at least 70%, at least 75%, at least 80%, at least 85%, at least 90%, at least 95%, at least 96%, at least 97%, at least 98%, at least 99% or 100% sequence identity to SEQ ID NOS: 2 or 3. In other embodiments, the diabodies possess the light and heavy chain of SEQ ID NOS: 2 and 3 or a sequence having at least 70%, at least 75%, at least 80%, at least 85%, at least 90%, at least 95%, at least 96%, at least 97%, at least 98%, at least 99% or 100% sequence identity to SEQ ID NOS: 2 or 3.

Diabodies, first described by Hollinger et al., PNAS (USA) 90(14): 6444-6448 (1993), may be constructed using heavy and light chains disclosed herein, as well as by using individual CDR regions disclosed herein. Typically, diabody fragments comprise a heavy chain variable domain (VH) connected to a light chain variable domain (VL) by a linker which is too short to allow pairing between the two domains on the same chain. Accordingly, the VH and VL domains of one fragment are forced to pair with the complementary VH and VL domains of another fragment, thereby forming two antigen-binding sites. Triabodies can be similarly constructed with three antigen-binding sites. An Fv fragment contains a complete antigen-binding site which includes a VL domain and a VH domain held together by non-covalent interactions. Fv fragments embraced by the present invention also include constructs in which the VH and VL domains are crosslinked through glutaraldehyde, intermolecular disulfides, or other linkers. The variable domains of the heavy and light chains can be fused together to form a single chain variable fragment (scFv), which retains the original specificity of the parent immunoglobulin. Single chain Fv (scFv) dimers, first described by Gruber et al., J. Immunol. 152(12):5368-74 (1994), may be constructed using heavy and light chains disclosed herein, as well as by using individual CDR regions disclosed herein. Many techniques known in the art can be used to prepare the specific binding constructs of the present invention (see, U.S. Patent Application Publication No. 20070196274 and U.S. Patent Application Publication No. 20050163782, which are each herein incorporated by reference in their entireties for all purposes, particularly with respect to minibody and diabody design).

Bispecific antibodies can be generated by chemical crosslinking or by the hybrid hybridoma technology. Alternatively, bispecific antibody molecules can be produced by recombinant techniques. Dimerization can be promoted by reducing the length of the linker joining the VH and the VL domain from about 15 amino acids, routinely used to produce scFv fragments, to about 5 amino acids. These linkers favor intrachain assembly of the VH and VL domains. Any suitable short linker can be used. Thus, two fragments assemble into a dimeric molecule. Further reduction of the linker length to 0-2 amino acids can generate trimeric (triabodies) or tetrameric (tetrabodies) molecules.

For preparation of antibodies, e.g., recombinant, monoclonal, or polyclonal antibodies, many techniques known in the art can be used (see, e.g., Kohler & Milstein, Nature 256:495-497 (1975); Kozbor et al., Immunology Today 4:72 (1983); Cole et al., in Monoclonal Antibodies and Cancer Therapy, Alan R. Liss, Inc., pp. 77-96 (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3.sup.rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., Nature 321:522-525 (1986); Riechmann et al., Nature 332:323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

Construction of suitable vectors containing the desired sequences and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to the full length of the reference sequence, usually about 25 to 100, or 50 to about 150, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher et al., J. Biol. Chem. 273(52):35095-35101 (1998).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Cancer" refers to human cancers and carcinomas, sarcomas, adenocarcinomas, etc., including solid tumors, kidney, breast, lung, kidney, bladder, urinary tract, urethra, penis, vulva, vagina, cervical, colon, ovarian, prostate, pancreas, stomach, brain, head and neck, skin, uterine, testicular, esophagus, and liver cancer.

Proliferative retinopathy refers to diabetic proliferative retinopathy caused by type I or II diabetes.

AMD or age-related macular degeneration refers to both wet and dry forms of the disease.

In any of the embodiments above, one or more chemotherapeutic drug and/or cancer therapy, e.g., radiation therapy can be administered further with the chimeric protein of the invention. In one embodiment the chimeric protein of the invention is administered in the same course of therapy as 5FU, leucovorin, oxaliplatin and/or irinolecan or any subcombination thereof. In some embodiments, the patient also receives hormone antagonist therapy. The contacting of the patient with the antibody or antibody fragment, can be by administering the antibody to the patient intravenously, intraperitoneally, intramuscularly, intratumorally, or intradermally.

The present chimeric, fusion proteins may act as a dual receptor antagonist. The term "dual antagonist" or "dual co-antagonist" as used herein refers to a peptide or a fusion protein fusion protein which is capable of inhibiting Ang2 and VEGF.

The present compositions include "Fc fragments" or "Fc regions." The term "Fc fragment" or "immunoglobulin Fc region" as used herein, refers to a protein that contains at least the heavy-chain constant region 2 (CH2) and the heavy-chain constant region 3 (CH3) of an immunoglobulin. In one embodiment, the Fc region excludes the variable regions of the heavy and light chains, the heavy-chain constant region 1 (CH1) and the light-chain constant region 1 (CL1) of the immunoglobulin. The Fc region may further include a hinge region at the heavy-chain constant region. Also, the immunoglobulin Fc region disclosed herein may contain a part or all of the Fc region including the heavy-chain constant region 1 (CH1) and/or the light-chain constant region 1 (CL1), except for the variable regions of the heavy and light chains, as long as it has a physiological function substantially similar to or better than the native protein. Also, the immunoglobulin Fc region may be a fragment having a deletion in a relatively long portion of the amino acid sequence of CH2 and/or CH3. That is, the immunoglobulin Fc region disclosed herein may comprise 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

The immunoglobulin Fc region disclosed herein includes a native amino acid sequence, or a sequence analogue thereof. An amino acid sequence analogue is a sequence that is different from the native amino acid sequence due to a deletion, an insertion, a non-conservative or conservative substitution or combinations thereof of one or more amino acid residues.

Also, other various analogues are possible, including one in which a region capable of forming a disulfide bond is deleted, or certain amino acid residues are eliminated at the N-terminal end of a native Fc form or a methionine residue is added thereto. Further, to remove effector functions, a deletion may occur in a complement-binding site, such as a C1q-binding site and an ADCC (antibody dependent cell mediated cytotoxicity) site. Techniques of preparing such sequence analogues of the immunoglobulin Fc region are disclosed in WO 1997/034631 and WO 1996/032478.

The aforementioned Fc analogues are analogues that have a biological activity identical to the Fc region disclosed herein or improved structural stability, for example, against heat, pH, or the like.

In addition, these Fc regions may be obtained from native forms isolated from humans and other animals including cows, goats, pigs, mice, rabbits, hamsters, rats and guinea pigs, or may be recombinants or analogues thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size exclusion chromatography to isolate Fc or pF'c. Preferably, a human-derived Fc region is a recombinant immunoglobulin Fc region that is obtained from a microorganism.

In one embodiment, the Fc region, if desired, may be modified by phosphorylation, sulfation, acrylation, glycosylation, methylation, farnesylation, acetylation, amidation, and the like. In one embodiment, the immunoglobulin Fc region disclosed herein may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc region results in a sharp decrease in binding affinity to the C1q part of the first complement component C1 and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable as a drug carrier.

As used herein, the term "deglycosylation" refers to enzymatically removing sugar moieties from an Fc region, and the term "aglycosylation" means that an Fc region is produced in an unglycosylated form by a prokaryote, preferably *E. coli*.

In one embodiment, the immunoglobulin Fc region may be an Fc region that is derived from IgG, IgA, IgD, IgE and IgM, or that is made by combinations thereof or hybrids thereof. Preferably, it is derived from IgG or IgM, which are among the most abundant proteins in human blood, and most preferably from IgG, which is known to enhance the half-lives of ligand-binding proteins.

The present chimeric fusion peptides may include a linker. In one embodiment, the linker is a peptide that ranges from about 6 to about 30 amino acids in length. In aspects of this embodiment, the peptide linker can be, e.g., at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or at least 30 amino acids in length. In other aspects of this embodiment, the peptide linker can be, e.g., at most 6, at most 7, at most 8, at most 9, at most 10, at most 11, at most 12, at most 13, at most 14, at most 15, at most 16, at most 17, at most 18, at most 19, at most 20, at most 21, at most 22, at most 23, at most 24, at most 25, at most 26, at most 27, at most 28, at most 29 or at most 30 amino acids in length. In other aspects of this embodiment, the peptide linker can be, e.g., about 6 to about 8, about 6 to about 10, about 6 to about 12, about 6 to about 14, about 6 to about 16, about 6 to about 18, about 6 to about 20, about 6 to about 22, about 6 to about 24, about 6 to about 26, about 6 to about 28, about 6 to about 30, about 8 to about 10, about 8 to about 12, about 8 to about 14, about 8 to about 16, about 8 to about 18, about 8 to about 20, about 8 to about 22, about 8 to about 24, about 8 to about 26, about 8 to about 28, about 8 to about 30, about 10 to about 12, about 10 to about 14, about 10 to about 16, about 10 to about 18, about 10 to about 20, about 10 to about 22, about 10 to about 24, about 10 to about 26, about 10 to about 28, about 10 to about 30, about 12 to about 14, about 12 to about 16, about 12 to about 18, about 12 to about 20, about 12 to about 22, about 12 to about 24, about 12 to about 26, about 12 to about 28, about 12 to about 30, about 14 to about 16, about 14 to about 18, about 14 to about 20, about 14 to about 22, about 14 to about 24, about 14 to about 26, about 14 to about 28, about 14 to about 30, about 16 to about 18, about 16 to about 20, about 16 to about 22, about 16 to about 24, about 16 to about 26, about 16 to about 28, about 16 to about 30, about 18 to about 20, about 18 to about 22, about 18 to about 24, about 18 to about 26, about 18 to about 28, about 18 to about 30, about 20 to about 22, about 20 to about 24, about 20 to about 26, about 20 to about 28, about 20 to about 30, about 22 to about 24, about 22 to about 26, about 22 to about 28, about 22 to about 30, about 24 to about 26, about 24 to about 28, about 24 to about 30, about 26 to about 28, about 26 to about 30 or about 26 to about 30 amino acids in length.

The term "native chemical ligation" (or NCL) as used herein refers to a concept for constructing a large polypeptide formed by the assembling of two or more unprotected peptides segments. Especially, NCL is the most powerful ligation method for synthesizing native backbone proteins or modified proteins.

The term "site specific conjugation" as used herein refers to a concept where a reaction group on a chemically synthesized peptide reacts specifically to a specific group of an Fc fragment produced through the recombinant technology. For example, a peptide contains an aldehyde group can react with the 1,2-aminothiol of cysteine of a recombinant Fc fragment through site-specific thiazolidine formation, as described by Zhang and Tam, "Thiazolidine formation as a general and site-specific conjugation method for synthetic peptides and proteins." Anal. Biochem. 1996 Jan. 1; 233(1): 87-93. Such chemically synthesized peptides may contain an aldehyde group. When the Fc region is chemically synthesized, the N-terminal amino acid of the Fc analogue may be modified to Cys, allowing site specific conjugation of the peptide to the Fc region.

The term "refolding" as used herein refers to the process by which a protein structure assumes its functional shape or conformation. It is the physical process by which a polypeptide folds into its characteristic and functional three-dimensional structure from random coil. It takes place at a basic pH (typically pH 8.0-10.0, pH 8.5-10, or pH 8.5-9.6), a low temperature (typically 0.0° C. to 10.0° C. or 2.0° C. to 8.0° C.), preferably with the presence of a redox pair at suitable concentrations, and/or at the presence of oxygen, and/or at the presence of catalyst(s) such as copper ions at suitable concentration.

The term "recombinant" as used herein refers to a polypeptide produced through a biological host, selected from a mammalian expression system, an insect cell expression system, a yeast expression system, and a bacterial expression system.

The term "formulation" as used herein refers to the fusion proteins disclosed herein and excipients combined together which can be administered and has the ability to bind to the corresponding receptors and initiate a signal transduction pathway resulting in the desired activity. The formulation can optionally comprise other agents so long as the fusion protein retains the ability to bind the corresponding receptors.

The present specification also provides a pharmaceutical composition for the administration to a subject. The pharmaceutical composition disclosed herein may further include a pharmaceutically acceptable carrier, excipient, or diluent. As used herein, the term "pharmaceutically acceptable" means that the composition is sufficient to achieve the therapeutic effects without deleterious side effects, and may be readily determined depending on the type of the diseases, the patient's age, body weight, health conditions, gender, and drug sensitivity, administration route, administration mode, administration frequency, duration of treatment, drugs used in combination or coincident with the composition disclosed herein, and other factors known in medicine.

The pharmaceutical composition including the fusion protein disclosed herein may further include a pharmaceutically acceptable carrier. For oral administration, the carrier may include, but is not limited to, a binder, a lubricant, a disintegrant, an excipient, a solubilizer, a dispersing agent, a stabilizer, a suspending agent, a colorant, and a flavorant. For injectable preparations, the carrier may include a buffering agent, a preserving agent, an analgesic, a solubilizer, an isotonic agent, and a stabilizer. For preparations for topical administration, the carrier may include a base, an excipient, a lubricant, and a preserving agent.

The disclosed compositions may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

On the other hand, examples of the carrier, the excipient, and the diluent suitable for the pharmaceutical formulations include, without limitation, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

Further, the pharmaceutical composition disclosed herein may have any formulation selected from the group consisting of tablets, pills, powders, granules, capsules, suspensions, liquids for internal use, emulsions, syrups, sterile aqueous solutions, non-aqueous solvents, lyophilized formulations and suppositories.

Further, the composition may be formulated into a single dosage form suitable for the patient's body, and preferably is formulated into a preparation useful for peptide drugs according to the typical method in the pharmaceutical field so as to be administered by an oral or parenteral route such as through skin, intravenous, intramuscular, intra-arterial, intramedullary, intramedullary, intraventricular, pulmonary, transdermal, subcutaneous, intraperitoneal, intranasal, intracolonic, topical, sublingual, vaginal, or rectal administration, but is not limited thereto.

The composition may be used by blending with a variety of pharmaceutically acceptable carriers such as physiological saline or organic solvents. In order to increase the stability or absorptivity, carbohydrates such as glucose, sucrose or dextrans, antioxidants such as ascorbic acid or glutathione, chelating agents, low molecular weight proteins or other stabilizers may be used.

The administration dose and frequency of the pharmaceutical composition disclosed herein are determined by the type of active ingredient, together with various factors such as the disease to be treated, administration route, patient's age, gender, and body weight, and disease severity.

The total effective dose of the compositions disclosed herein may be administered to a patient in a single dose, or may be administered for a long period of time in multiple doses according to a fractionated treatment protocol. In the pharmaceutical composition disclosed herein, the content of active ingredient may vary depending on the disease severity. Preferably, the total daily dose of the peptide disclosed herein may be approximately 0.0001 μg to 500 mg per 1 kg of body weight of a patient. However, the effective dose of the peptide is determined considering various factors including patient's age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition disclosed herein. The pharmaceutical composition disclosed herein is not particularly limited to the formulation, and administration route and mode, as long as it shows suitable effects.

The pharmaceutical composition disclosed herein is expected to have longer in-vivo duration of efficacy and titer, thereby remarkably reducing the number and frequency of administration thereof.

Moreover, the pharmaceutical composition may be administered alone or in combination or coincident with other pharmaceutical formulations showing prophylactic or therapeutic efficacy.

In still another aspect, the present specification provides a method for preventing or treating of cancer, proliferative retinopathies, AMD and RA and related diseases comprising the step of administering to a subject the chimeric protein or the pharmaceutical composition including the same.

As used herein, the term “prevention” means all of the actions by which the occurrence of the disease is restrained or retarded.

As used herein, the term “treatment” means all of the actions by which the symptoms of the disease have been alleviated, improved or ameliorated. In the present specification, “treatment” means that the symptoms cancer, proliferative retinopathy, AMD or RA are alleviated, improved or ameliorated by administration of the fusion proteins disclosed herein.

As used herein, the term “administration” means introduction of an amount of a predetermined substance into a patient by a certain suitable method. The composition disclosed herein may be administered via any of the common routes, as long as it is able to reach a desired tissue, for example, but is not limited to, intraperitoneal, intravenous, intramuscular, subcutaneous, intradermal, oral, topical, intranasal, intrapulmonary, or intrarectal administration. However, since peptides are digested upon oral administration, active ingredients of a composition for oral administration should be coated or formulated for protection against degradation in the stomach.

In the present specification, the term “subject” is those suspected of having cancer, proliferative retinopathies, AMD or RA. However, any subject to be treated with the fusion proteins or the pharmaceutical composition disclosed herein is included without limitation. The pharmaceutical composition including the fusion peptide disclosed herein is administered to a subject suspected of having cancer, proliferative retinopathies, AMD or RA.

The therapeutic method of the present specification may include the step of administering the composition including the fusion protein at a pharmaceutically effective amount. The total daily dose should be determined through appropriate medical judgment by a physician, and administered once or several times. The specific therapeutically effective dose level for any particular patient may vary depending on various factors well known in the medical art, including the kind and degree of the response to be achieved, concrete compositions according to whether other agents are used therewith or not, the patient’s age, body weight, health condition, gender, and diet, the time and route of administration, the secretion rate of the composition, the time period of therapy, other drugs used in combination or coincident with the composition disclosed herein, and like factors well known in the medical arts.

In still another aspect, the present specification provides a use of the therapeutic protein or the pharmaceutical composition including the same in the preparation of drugs for the prevention or treatment of cancer, proliferative retinopathies, AMD or RA and related diseases.

In one embodiment, the dose of the composition may be administered daily, semi-weekly, weekly, bi-weekly, or monthly. The period of treatment may be for a week, two weeks, a month, two months, four months, six months, eight months, a year, or longer. The initial dose may be larger than a sustaining dose. In one embodiment, the dose ranges from a weekly dose of at least 0.01 mg, at least 0.25 mg, at least 0.3 mg, at least 0.5 mg, at least 0.75 mg, at least 1 mg, at least 1.25 mg, at least 1.5 mg, at least 2 mg, at least 2.5 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 50 mg, at least 55 mg, at least 60 mg, at least 65 mg, or at least 70 mg. In one embodiment, a weekly dose may be at most 0.5 mg, at most 0.75 mg, at most 1 mg, at most 1.25 mg, at most 1.5 mg, at most 2 mg, at most 2.5 mg, at most 3 mg, at most 4 mg, at most 5 mg, at most 6 mg, at most 7 mg, at most 8 mg, at most 9 mg, at most 10 mg, at most 15 mg, at most 20 mg, at most 25 mg, at most 30 mg, at most 35 mg, at most 40 mg, at most 50 mg, at most 55 mg, at most 60 mg, at most 65 mg, or at most 70 mg. In a particular aspect, the weekly dose may range from 0.25 mg to 2.0 mg, from 0.5 mg to 1.75 mg. In an alternative aspect, the weekly dose may range from 10 mg to 70 mg.

EXAMPLES

Example 1—Production of the Chimeric Molecule Comprising VEGF Antibody and Ang2 Binding Peptide in HEK293 Cells Chimeric molecules named AMD A, B, C, D and E (see Table 1) were expressed through transient expression by HEK-293 cells. Briefly, DNAs (SEQ ID NOS: 20, 21, 22 and 25) for the fusion proteins comprising VEGF antibody light chain with or without Ang2 binding peptides and DNAs (SEQ ID NOS: 19, 23 and 24) for the fusion proteins comprising VEGF antibody heavy chain with Ang2 binding peptides were synthesized and cloned into expression vectors. The complete expression constructs comprising the genes were confirmed by DNA sequencing. DNA constructs were transformed into *E. coli* DH5alfa competent cells (Invitrogen). Single clone was selected and cultured in LB broth with antibiotics (kanamycin, 25 ug/mL). DNA plasmids were extracted with Qiagen Plasmid Maxi Kit (Qiagen) following manufacture’s protocol. Plasmid concentration was measured by NanoDrop (Thermo Fisher). The expression plasmid constructs containing the DNA sequences encoding the genes of interest, were introduced into HEK-293 cells transiently by using polyethylenimine (PEI). The transfected cells were treated by alproic acid (VPA) 24 hours post transfection to enhance protein expression.

TABLE 1

| AMD Molecules | | | | | |
|---|---|---|---|---|---|
| | AMD-A | AMD-B | AMD-C | AMD-D | AMD-E |
| Light Chain | Peptide L1-15 (No LE*) fused to N-terminus of Bevacizumab light chain | Bevacizumab light chain | Peptide L1-15 (with LE) fused to N-terminus of Bevacizumab light chain | Bevacizumab light chain | Bevacizumab light chain |
| Light Chain DNA SEQ ID NO | SEQ ID NO: 21 (LY2.55.1) | SEQ ID NO: 25 (LY2.55.5) | SEQ ID NO: 22 (LY2.55.2) | SEQ ID NO: 25 (LY2.55.5) | SEQ ID NO: 20 (DHAMDL083016) |
| Heavy Chain | Peptide L1-15 (No LE) fused to N-terminus of Bevacizumab heavy chain | Peptide L1-15 (No LE) fused to N-terminus of Bevacizumab heavy chain | Peptide L1-15 (with LE) fused to N-terminus of Bevacizumab heavy chain | Peptide L1-15 (with LE) fused to N-terminus of Bevacizumab heavy chain | Peptide 2xCon4(C) fused to the C-terminus of the Heavy Chain of Bevacizumab |
| Heavy Chain DNA SEQ ID NO | SEQ ID NO: 23 (LY2.55.3) | SEQ ID NO: 23 (LY2.55.3) | SEQ ID NO: 24 (LY2.55.4) | SEQ ID NO: 24 (LY2.55.4) | SEQ ID NO: 19 (DHAMDH02083016) |

*LE is one of the flanking sequences, which were present both in the original phage clone when the peptides were screened and in the subsequent peptibody (Peptide-Fc fusion) molecules.

After approximately 6 days of culturing, the cell culture media were harvested by clarifying centrifugation at 9000 rpm for 30-60 minutes followed by filtration through 0.22 micrometer filters. The clarified supernants were loaded to a Protein A affinity column and the chimeric molecules (AMD-A, B, C, D and E) were purified. The chimeric molecules were eluted using 2 M arginine solution, pH 4 from the protein A column. FIG. 1 shows a representative chromatograph of the Protein A column step. Table 2 summarizes the results from the purification of the chimeric molecules. As shown in Table 2, chimeric molecules containing a total of 2 copies L1-15 peptides (AMD-B and AMD-D), both fused to the N-terminals of the heavy chain, had significantly higher expression levels comparing to the ones with a total of four copies of L1-15 peptides (AMD-A and AMD-C), wherein there is one each of L1-15 peptide fused to the N-terminals of both the light chains and the heavy chains of the antibody. With or without the flanking sequence LE as part of the L1-15 peptide did not appear to affect the expression of the chimeric molecules.

The expression level of AMD-E was comparable to that of AMD-B and AMD-D (Table 2). AMD-E has one Peptide 2×Con4(C) fused to each of the C-terminus of the heavy chains of Bevacizumab. The purity of the products were analyzed using SDS electrophoresis and/or HPLC methods.

TABLE 2

| Summary of Protein A Affinity Chromatography Purification | | | | | |
|---|---|---|---|---|---|
| | AMD-A | AMD-B | AMD-C | AMD-D | AMD-E |
| Approximate culture volume (ml) | 150 | 200 | 150 | 150 | 200 |
| Protein A Pool Volume (ml) | 3 | 9 | 5 | 12 | 17 |
| OD280 | 0.24 | 1.14 | 0.29 | 0.88 | 0.80 |
| Approximate amount in the Protein A Pool, (mg) | 0.45 | 6.4 | 0.91 | 6.6 | 8.5 |

Example 2—Production of the Chimeric Molecule Comprising VEGF Trap and Ang2 Binding Peptide in CHO Cells DNA for the chimeric molecule comprising the VEGF Receptor-Fc fusion protein (VEGF Trap) and the Ang2 binding peptide (SEQ ID NO:6, named as ASKB-E06) is synthesized and cloned into an expression vector. The complete expression construct comprising the DNA gene is confirmed by DNA sequencing. The expression construct is amplified by transforming into DH10B *E. coli* and culturing the cells overnight. DNA for the expression construct was prepared and purified by endo-free plasmid kit (from QIAGEN®).

Cell lines stably expressing ASKB-E06 is obtained by transfecting the expression construct into $GS^{-/-}$ Chinese hamster ovarian cells (CHO) by electroporation and screening for transfected CHO cells using a selective culture medium without glutamine (EX-CELL® CD CHO Fusion Growth Medium). In this manner 32 or more stable mini-pools are established and the leading mini-pool is selected based on expression level in batch and fed-batch cultures. The expression levels are detected by ELISA titer assay. Single cloning is performed by limited dilution and using clone media, two leading single clones out of more than 100 positive clones are selected based on productivity and cell growth in batch and fed-batch culture. The lead clones are expanded and seeded at $0.5\times10^6$ cells/mL, total 300 mL in 2 L shake flasks, and the cells are cultured at 37° C., 5% $CO_2$, 70% HMR conditions and shaking at 120 rpm. The cultures are fed by using 5% Acti CHO® Feed A+0.5% Feed B (from GE Health) on Day 3, 6, 7, 8 and 9. The cell viability, viable cell density are monitored every other day, the cultures are harvested on Day 11-13.

The cell culture medium is harvested by clarifying approximately 600 mL of the cultured cell medium through centrifugation at 2000 rpm for 10 minutes followed by filtration. The clarified supernant is loaded to a Protein A affinity column and the chimeric molecule is purified. The protein is further purified using ion exchange chromatography, hydrophobic interaction chromatography, hydroxyapatite chromatography, and/or mixed mode chromatography. The product is further concentrated and buffer exchanged using UFDF and further formulated. The purity of the product is analyzed using CE-SDS and HPLC methods.

Figure 2:
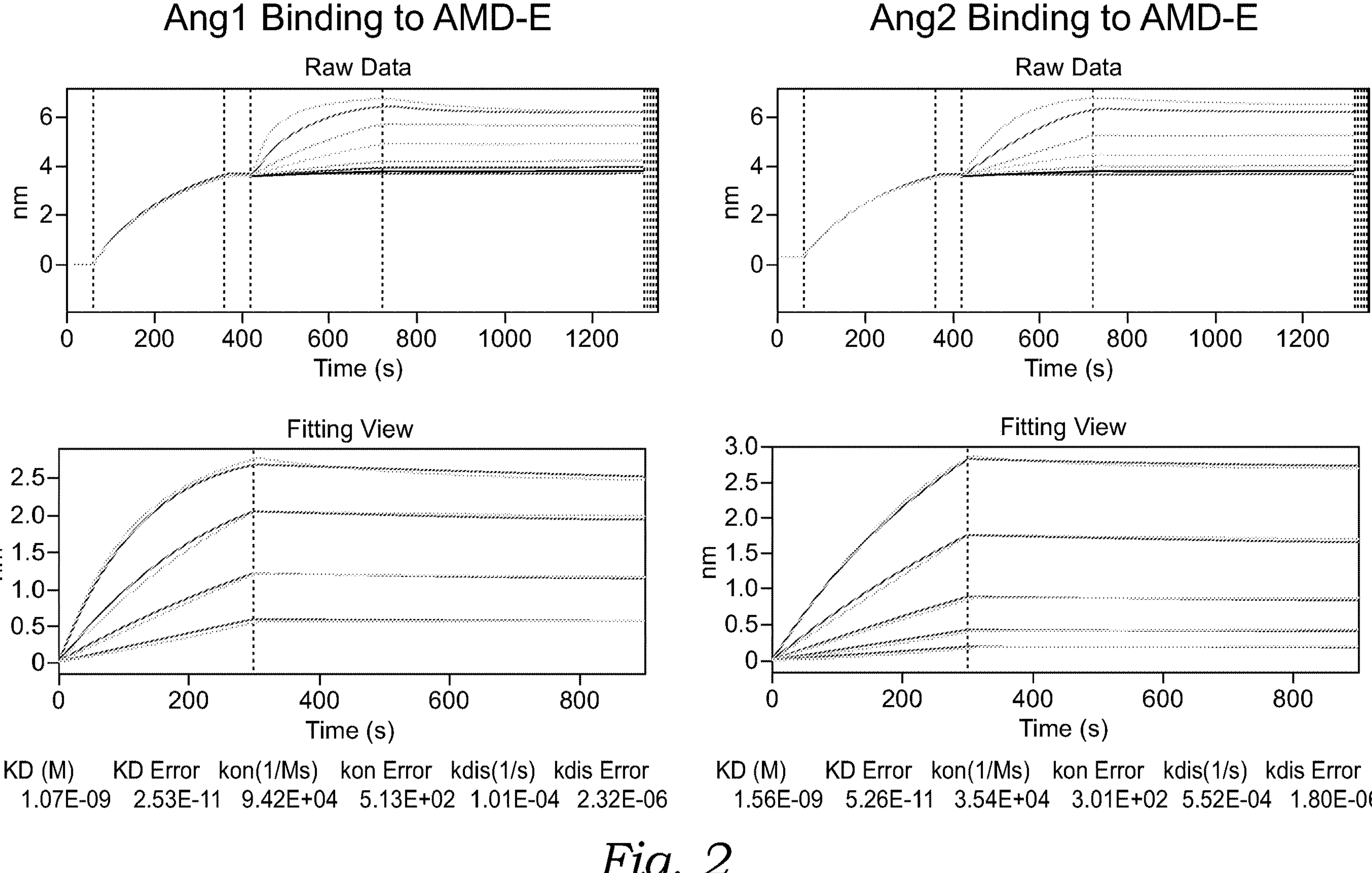
FIG. 2. Kinetics of Ang-1 or Ang-2 Binding to AMD-E As Analyzed by Octet Red96.

Example 3—Molecular Assays to Evaluate Dual Antagonist Activities of the Chimeric Molecules Molecular assays (Octet Binding Affinity, Affinity ELISA, and Blocking ELISA) were developed to assess direct binding of the chimeric molecules to ANG-1, Ang-2 and/or VEGF, and the effect of the chimeric molecules on the Ang1:Tie-2 interaction, Ang-2:Tie-2 interaction and/or VEGF:VEGF receptor interaction. These in vitro assays are described as the following:

Octet Affinity: Purified recombinant human VEGF protein was ordered from Life-Technologies (Cat. #PHC9391). Human Ang1 or Ang2 protein were ordered from R&D System. Analysis was carried out using Octet Red96 from Pall ForteBio. Using anti-human IgG Fc sensors, a sample of chimeric molecule AMD-B, AMD-D, AMD-E or the control antibody Bevacizumab was loaded for 300 seconds at 3 ug/mL in the kinetics buffer. Ligands ANG1, ANG2, or VEGF samples were associated for 300 seconds using a dilution series starting at 5 or 10 ug/mL and sequentially diluting 2-fold for 7 wells. Dissociation was run for 600 seconds. Data was analyzed using a 1:1 model with global fit. A representative binding kinetics graph is shown in FIG. 2. The binding affinity results are summarized in Tables 3A, 3B and 3C. The results showed that the chimeric molecules AMD-B, AMD-D, and AMD-E were able to bind to Ang1, Ang2, and VEGF. It was also noticed that the chimeric molecule AMD-B with four L1-15 peptides fused to the N-terminals of the antibody had reduced affinity to VEGF when comparing to the control antibody Bevacizumab. AMD-D and AMD-E showed comparable affinity to VEGF comparing to the control antibody ASKB1202, a biosimilar m An internal control, ASKB 1202, a biosimilar to Bevacizumab developed in-house.

TABLE 3A

Summary of the Octet Affinity analysis results - Binding of ANG-1.

| | kon (1/Ms) | koff (1/s) | KD (M) |
|---|---|---|---|
| AMD-B | 1.56E+05 | 2.69E−04 | 1.73E−09 |
| AMD-D | 1.75E+05 | 2.41E−04 | 1.37E−09 |
| AMD-E | 9.42E+04 | 1.01E−04 | 1.07E−09 |

TABLE 3B

Summary of the Octet Affinity analysis results - Binding of ANG-2.

| | kon (1/Ms) | koff (1/s) | KD (M) |
|---|---|---|---|
| AMD-B | 3.34E+04 | 4.33E−05 | 1.30E−09 |
| AMD-D | 3.68E+04 | 2.39E−05 | 6.49E−10 |
| AMD-E | 3.54E+04 | 5.52E−05 | 1.56E−09 |

TABLE 3C

Summary of the Octet Affinity analysis results - Binding of VEGF.

| | kon (1/Ms) | koff (1/s) | KD (M) |
|---|---|---|---|
| Bevacizumab | 8.03E+04 | <1.0E−07 | <1.0E−12 |
| AMD-B | 1.41E+05 | 3.42E−05 | 2.42E−10 |
| AMD-D | 1.01E+05 | <1.0E−07 | <1.0E−12 |
| AMD-E | 1.38E+05 | <1.0E−07 | <1.0E−12 |

Affinity ELISA: Purified recombinant human VEGF protein was ordered from Life-Technologies (Cat. #PHC9391). VEGF is reconstituted in BSA solution at 0.1 mg/mL as recommended by the manufacturer. Aliquots the samples were made and stored at −20° C.

Using microtiter plates, approximately 100 microliters per well of VEGF is added to each well and the plates were incubated about 2 hours, after which the plates are washed with phosphate buffered saline (PBS) containing about 0.1 percent Tween-20 four times. The wells are then blocked using about 250 microliters per well of about 5 percent BSA in PBS, and the plates were incubated at room temperature for about 2 hours. After incubation, excess blocking solution is discarded, and about 100 microliters of AMD-A, B, C, D or E was added to a well in a dilution series starting at a concentration of about 40 nanomolar and then serially diluting 4-fold in PBS containing about 1 percent BSA. The plates were then incubated overnight at room temperature. After incubation, plates were washed with PBS containing about 0.1 percent Tween-20. Washing was repeated four additional times, after which about 100 microliters per well of goat anti-human IgG(Fc)-HRP (Pierce Chemical Co., catalog #31416) previously diluted 1:5000 in PBS containing 1 percent BSA was added. Plates were incubated approximately 1 hour at room temperature. Plates were then washed five times in PBS containing about 0.1 percent Tween-20, after which about 100 microliters per well of TMB (3,3',5,5'-Tetramethylbenzidine Liquid Substrate System; Sigma Chemical Company, St. Louis, MO, catalog number T8665) substrate was added and plates are incubated about 5-15 minutes until blue color developed. Absorbance was then read in a spectrophotometer at about 450 nm.

Figure 3:
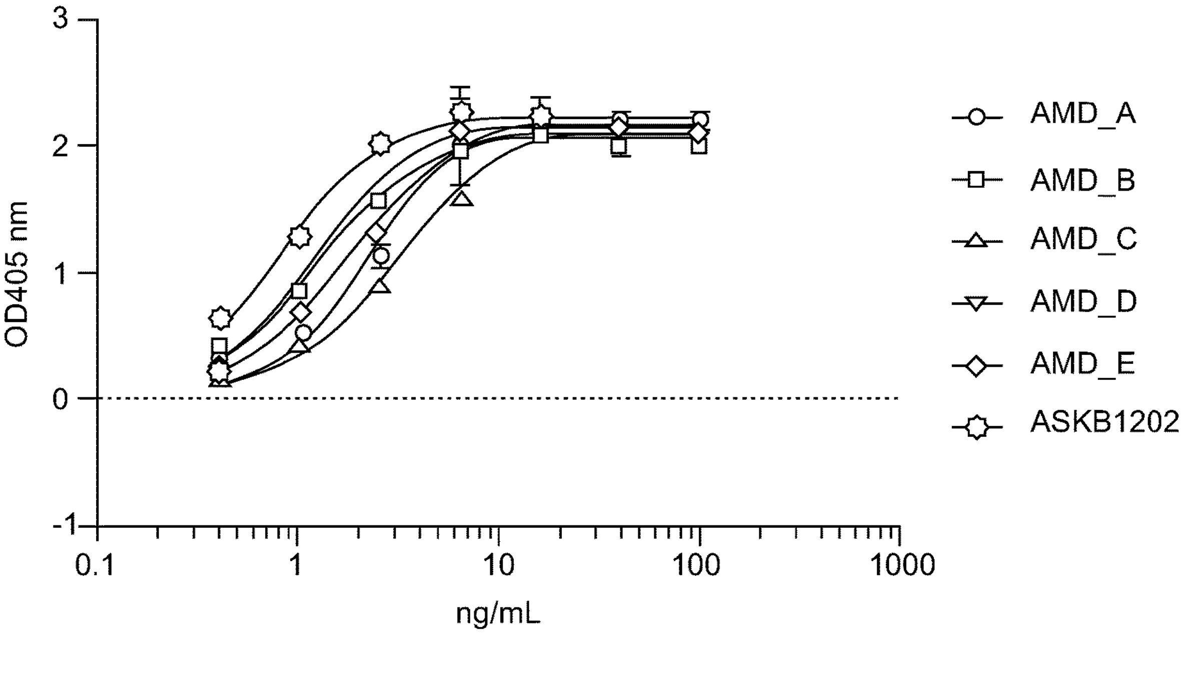
FIG. 3. Blocking of Binding of Ang-1 and Ang-2 to Tie-2 by AMD-E.

FIG. 3 shows the ELISA results of binding of VEGF to AMD-A, B, C, D, and E. An internal control, ASKB 1202, a biosimilar to Bevacizumab currently in development, was used as a positive control. The results showed that all the molecules AMD-A, B, C, D and E retained abilities to bind to VEGF. The EC-50 results are summarized in Table 4. The results showed that the AMD-B and AMD-D had VEGF binding affinity close to ASKB1202. In addition, AMD-B and AMD-D had stronger VEGF binding affinity than AMD-A and AMD-C.

TABLE 4

Affinity ELISA Results: Binding of VEGF to AMD-A, B, C, D and E.

| | EC-50 (ng/ml) |
|---|---|
| AMD-A | 2.296 |
| AMD-B | 1.278 |
| AMD-C | 3.328 |
| AMD-D | 1.247 |
| AMD-E | 1.87 |
| ASKB1202 | 0.8002 |

Blocking ELISA: The chimeric molecules were assessed in their abilities in blocking the binding of Ang1 and Ang2 to their receptor Tie-2. 96 well microtiter plate (Nunk) was coated with 100 uL final concentration 100 ng/mL of human Tie2-Fc (R&D System, 313-T1) diluted in 0.1 M carbonate (pH9.3) at 4° C. overnight. The plate was then blocked for 2 hours with 5% BSA in PBST (0.05% Tween 20). Purified chimeric molecule, at starting concentration of 1000 ng/mL, was serially diluted with dilution factor of three in PBS with 1% BSA. Human Ang1 or Ang2 protein (R&D System) was added to final concentration of 50 ng/mL and incubated at room temperature for 1 hour. The Chimeric molecule-Ang1 or Chimeric molecule-Ang2 mixture was then added into microtiter plate coated with human Tie2-Fc and incubate for another 1 hour at room temperature. 100 uL anti-Ang1 or anti-Ang2 monoclonal antibody (R&D System) was added into each well at final concentration of 1 ug/mL and incubated for 1 hour at room temperature. Horseradish-peroxidase (HRP) conjugated anti-mouse IgG secondary antibody was added at 1:5000 dilution and incubated for 1 hour at room temperature. Standard colorimetric response was developed by using TMB (Pierce). Absorbance was read at OD450 by spectrophotometer. Between each step, the plate was washed 5 time with 100 uL PBS.

Figure 4A:
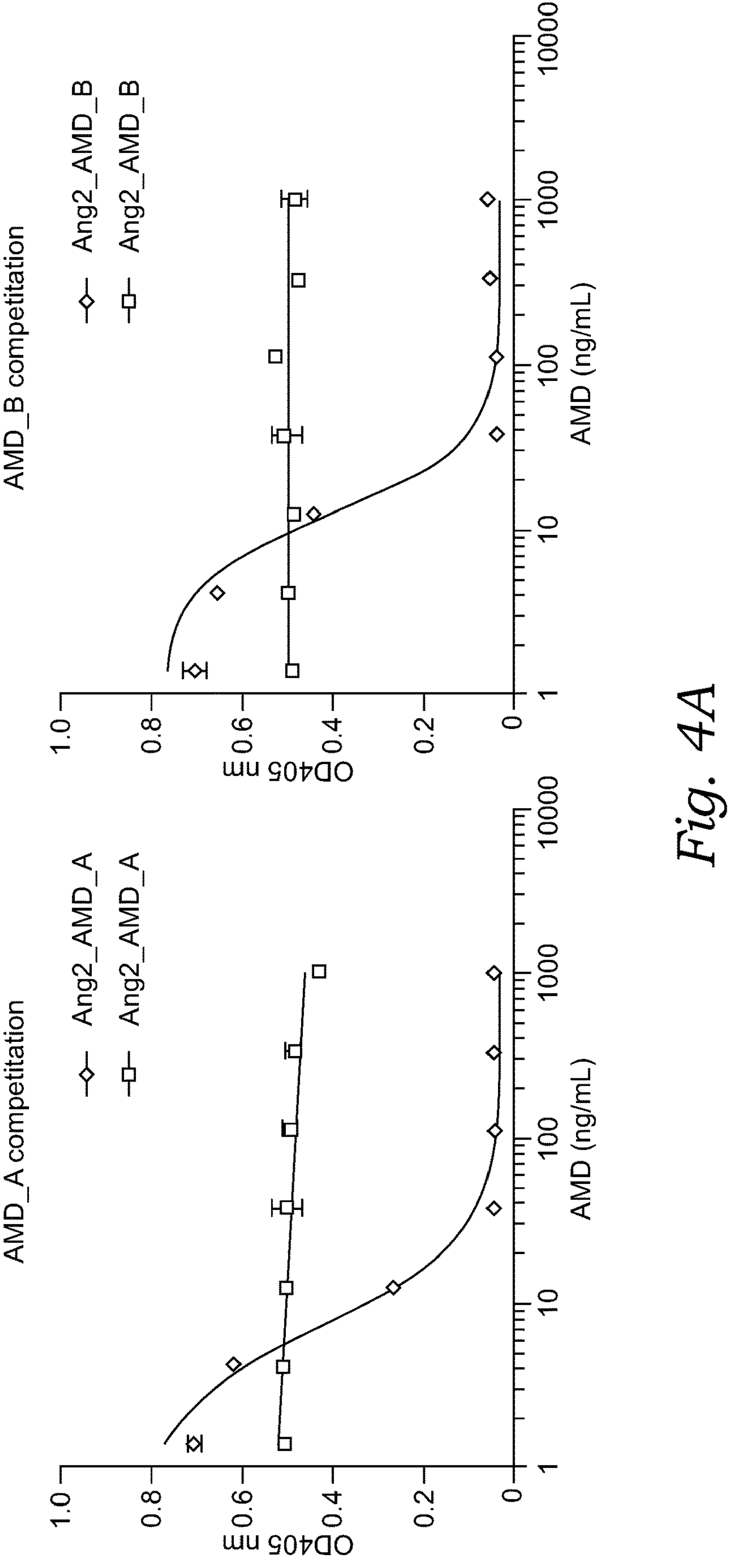
FIG. 4A. Blocking of Binding of Ang-1 and Ang-2 to Tie-2 by AMD-A and AMD-B.
Figure 4B:
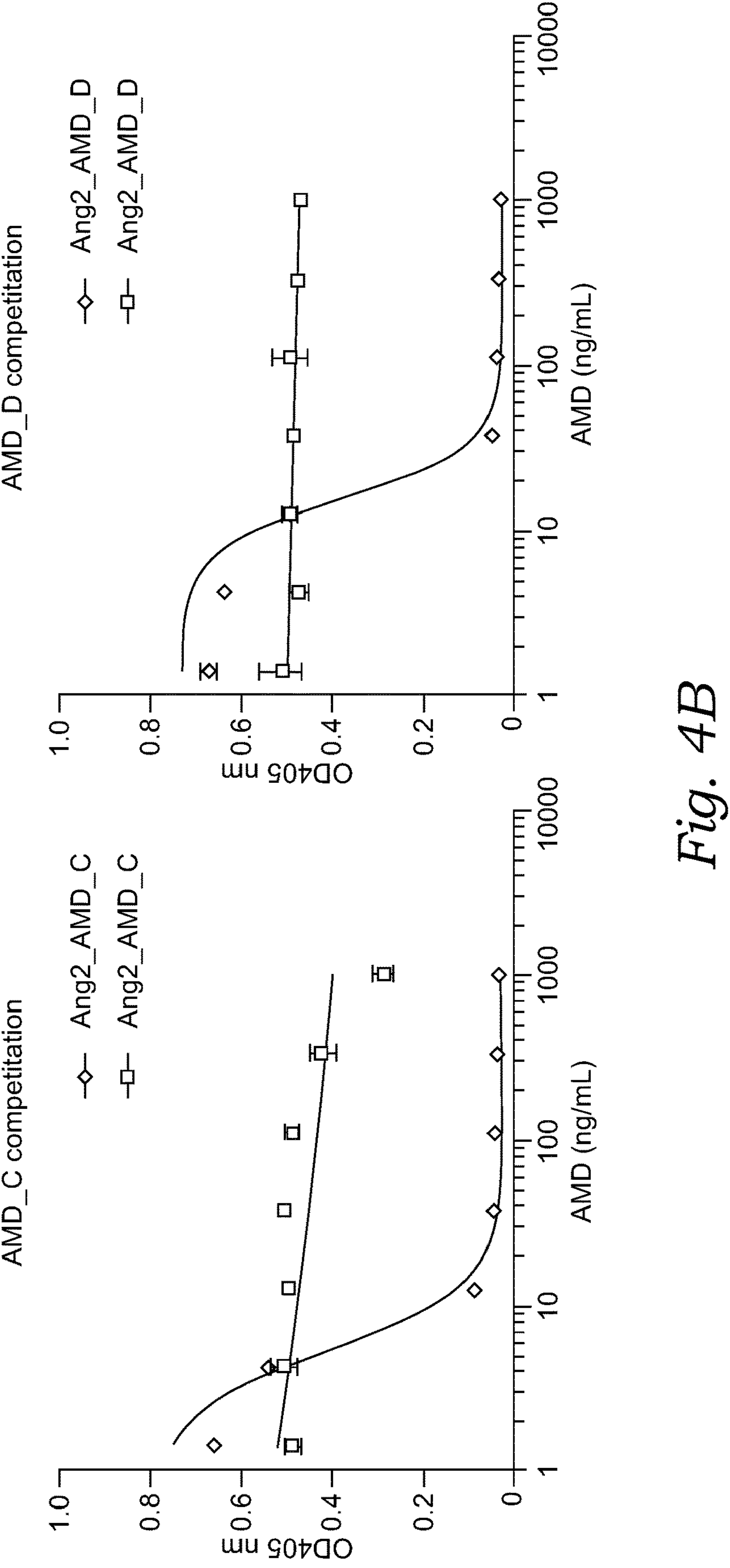
FIG. 4B. Blocking of Binding of Ang-1 and Ang-2 to Tie-2 by AMD-C and AMD-D.

The dose dependent inhibition or lack of inhibition of the binding of Ang1 and Ang-2 to receptor Tie-2 are shown in FIG. 4. The IC-50 results are summarized in Table 5. The results showed that the chimeric molecules AMD-A, B, C, and D selectively inhibited the binding of Ang2 to Tie-2, with IC-50 in the range of 5-15 ng/ml; while their abilities in inhibiting the binding of Ang-1 to Tie-2 were very weak, if any, despite the fact that they all were able to bind to Ang1. The results also showed that AMD-A and AMD-C, both comprising 4 copies of the peptide L1-15 had lower IC-50 than AMD-B and AMD-D. AMD-E was able to inhibit the association of both Ang-1 and Ang-2 to their receptor Tie-2.

TABLE 5

Blocking ELISA Results: Inhibition of Binding of Ang-1 or Ang-2 to Tie-2.

| | IC-50 of inhibiting Ang-1 Binding (ng/ml) | IC-50 of Inhibiting Ang-2 Binding (ng/ml) |
|---|---|---|
| AMD-A | Not detected | 7.3 |
| AMD-B | Not detected | 12.49 |
| AMD-C | Not detected | 5.136 |
| AMD-D | Not detected | 15.21 |
| AMD-E | 10 (estimated) | 2.107 |

Example 4—Cell-Based Activity Assay: In Vitro Human Umbilical Vein Endothelial Cells (HUVEC) Tube-Formation Assay In order to confirm whether or not ASKB-E06 inhibits angiogenesis, proliferation, migration, and differentiation assays of human umbilical vein endothelial cells (HUVEC) are performed.

(1) Proliferation Inhibition of HUVEC by ASKB-E06

After 10,000 HUVEC were added to 100 μl of EBM-2 medium (Lonza, Switzerland), EBM-2 medium having VEGF-A (50 ng/ml) is added thereto, or EBM-2 medium including VEGF-A (50 ng/ml) and ASKB-E06 sample at different concentration is added thereto in each well of a 96-well plate, followed by incubation under 5% $CO_2$, at 37° C. for 72 hours. Then, 10 μl of WST-1 solution was added thereto, followed by incubation at 37° C. for 4 hours. Absorbance is measured at 410 nm with a reference of 610 nm.

(2) Migration Inhibition of HUVEC by ASKB-E06

After a bottom of Transwells, (Corning Inc., US) having a pore size of 8-μm is coated with 0.1% gelatin and mounted in a 24-well plate, a lower chamber is filled with 600 μl of EBM-2 medium (Lonza), EBM-2 with VEGF-A (50 ng/ml), or EBM-2 with VEGF-A (50 ng/ml) and ASKB-E06 sample at different concentration. An upper chamber is provided with 100 μl of EBM-2 medium containing $1\times10^5$ HUVEC. After incubation in 37° C. cell incubator for 4 hours, a filter is detached from the Transwell and cells are fixed with methanol for 1 minute and stained with Hematoxylin/Eosin. Cells which do not migrate but are left on an upper surface of the transwell are completely removed with a cotton swab. Five random fields among the cells migrated through the filter are arbitrarily chosen under an optical microscope (×100) and the number thereof is counted.

(3) Inhibition of Tube Formation by ASKB-E06

In order to confirm that ASKB-E06 can inhibit differentiation of HUVEC, tube formation assay is performed. More specifically, after a 96-well plate is coated with Growth Factor Reduced Matrigel (BD Biosciences, US), 15,000 HUVEC in 100 μl of EBM-2 medium, EBM-2 medium with VEGF-A (50 ng/ml), or EBM-2 medium with VEGF-A (50 ng/ml) and an antibody sample are added to each well, followed by incubation in 37° C. cell incubator for 6 hours. Then, tube formation is observed by using an inverted microscope.

Example 5—In Vivo Anti-Tumor Activity Study: Therapeutic Efficacy Studies with Systemically Administered Dual Antagonist Chimeric Molecules The chimeric molecule ASKB-E06 is administered subcutaneously to A431 tumor-bearing mice at a once-per-day schedule 72 hours after tumor challenge. The doses used are 1000, 200, 40 and 8 ug/mouse/day. A total of 20 doses is given to all animals. Tumor volumes and body weights are recorded three times/week. At the end of the study, animals are sacrificed, and their sera are collected for measuring ASKB-E06 levels by ELISA. Tumors and a panel of normal tissues are collected from all groups.

The following non-limiting examples are provided for illustrative purposes only in order to facilitate a more complete understanding of the disclosed subject matter. These examples should not be construed to limit any of the embodiments described in the present specification, including those pertaining to the fusion peptides, pharmaceutical compositions, or methods and uses for treating cancer, proliferative retinopathies, AMD or RA.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

SEQUENCES

```
SEQ ID NO: 1, 2xCon4(C) (Ang2 peptide)
(1)     10          20          30          40          50
    GGGGGAQQEE CEWDPWTCEH MGSGSATGGS GSTASSGSGS ATHQEECEWD PWTCEHMLE

SEQ ID NO: 2, Bevacizumab Heavy Chain
(1)     10          20          30          40          50          60
    EVQLVESGGG LVQPGGSLRL SCAASGYTFT NYGMNWVRQA PGKGLEWVGW INTYTGEPTY

            70          80          90         100         110         120
    AADFKRRFTF SLDTSKSTAY LQMNSLRAED TAVYYCAKYP HYYGSSHWYF DVWGQGTLVT

           130         140         150         160         170         180
    VSSASTKGPS VFPLAPSSKS TSGGTAALGC LVKDYFPEPV TVSWNSGALT SGVHTFPAVL

           190         200         210         220         230         240
    QSSGLYSLSS VVTVPSSSLG TQTYICNVNH KPSNTKVDKK VEPKSCDKTH TCPPCPAPEL

           250         260         270         280         290         300
    LGGPSVFLFP PKPKDTLMTS RTPEVTCVVV DVSHEDPEVK FNWYVDGVEV HNAKTKPREE

           310         320         330         340         350         360
    QYNSTYRVVS VLTVLHQDWL NGKEYKCKVS NKALPAPIEK TISKAKGQPR EPQVYTLPPS

           370         380         390         400         410         420
    REEMTNKQVS LTCLVKGEYP SDIAVEWESN GQPENNYKTT PPVLDSDGSF FLYSKLTVDK

           430         440         450
    SRWQQGNVFS CSVMHEALHN HYTQKSLSLS PGK


SEQ ID NO: 3, Bevacizumab Light Chain
(1)     10          20          30          40          50          60
    DIQMTQSPSS LSASVGDRVT ITCSASQDIS NYLNWYQQKP GKAPKVLIYF TSSLHSGVPS

            70          80          90         100         110         120
    RFSGSGSGTD FTLTISSLQP EDFATYYCQQ YSTVPWTFGQ GTKVEIKPTV AAPSVFIFPP

           130         140         150         160         170         180
    SDEQLKSGTA SVVCLLNNFY PREAKVQWKV DNALQSGNSQ ESVTEQDSKD STYSLSSTLT

           190         200         210
    LSKADYEKHK VYACEVTHQG LSSPVTKSFN RGEC

SEQ ID NO: 4, 2xCon4(C) fused to the C-terminus of the Heavy Chain
of Bevacizumab
(1)     10          20          30          40          50          60
    EVQLVESGGG LVQPGGSLPL SCAASGYTFT NYGMNWVRQA PGKGLEWVGW INTYTGEPTY

            70          80          90         100         110         120
    AADFKRRFTF SLDTSKSTAY LQMNSLRAED TAVYYCAKYP HYYGSSHWYF DVWGQGTLVT

           130         140         150         160         170         180
    VSSASTKGPS VFPLAPSSKS TSGGTAALGC LVKDYFPEPV TVSWNSGALT SGVHTFPAVL

           190         200         210         220         230         240
    QSSGLYSLSS VVTVPSSSLG TQTYICNVNH KPSNTKVDKK VEPKSCDKTH TCPPCPAPEL

           250         260         270         280         290         300
    LGGPSVFLFP PKPKDTLMIS RTPEVTCVVV DVSHEDPEVK FNWYVDGVEV HNAKTKPREE

           310         320         330         340         350         360
    QYNSTYRVVS VLTVLHQDWL NGKEYKCKVS NKALPAPIEK TISKAKGQPR EPQVYTLPPS

           370         380         390         400         410         420
    REEMTKNQVS LTCLVKGFYP SDIAVEWESN GQPENNYKTT PPVLDSDGSF FLYSKLTVDK
```

-continued

| SEQUENCES |
|---|

```
       430        440        450        460        470        480
SPWQQGNVFS CSVMHEALHN HYTQKSLSLS PGKGGGGGAQ QEECEWDPWT CEHMGSGSAT

       490        500        510
GGSGSTASSG SGSATHQEEC EWDPWTCEHM LE
```

SEQ ID NO: 5, VEGF Trap Aflibercept

```
(1)  10         20         30         40         50         60
SDTGRPFVEM YSEIPEIIHM TEGRELVIPC RVTSPNITVT LKKFPLDTLI PDGKRIIWDS

        70         80         90        100        110        120
RKGFIISNAT YKEIGLLTCE ATVNGHLYKT NYLTHPQTNT IIDVVLSPSH GIELSVGEKL

       130        140        150        160        170        180
VLNCTARTEL NVGIDFNWEY PSSKHQHKKL VNRDLKTQSG SEMKKFLSTL TIDGVTRSDQ

       190        200        210        220        230        240
GLYTCAASSG LMTKKNSTFV RVHEKDKTHT CPPCPAPELL GGPSVFLFPP KPKDTLMISP

       250        260        270        280        290        300
TPEVTCVVVD VSHEDPEVKF NWYVDGVEVK NAKTKPREEQ YNSTYRVVSV LTVLHQDWLN

       310        320        330        340        350        360
GKEYKCKVSN KALPAPIEKT ISKAKGQPRE PQVYTLPPSR DELTKNQVSL TCLVKGFYPS

       370        380        390        400        410        420
DIAVEWESNG QPENNYKTTP PVLDSDGSFF LYSKLTVDKS RWQQGNVFSC SVMHEALHNH

       430
YTQKSLSLSP G(K)
```

SEQ ID NO: 6, 2xCon4(C) fused to the C-terminus of the VEGF Trap

```
(1)  10         20         30         40         50         60
SDTGRPFVEM YSEIPEIIHM TEGRELVIPC RVTSPNITVT LKKFPLDTLI PDGKRIIWDS

        70         80         90        100        110        120
PKGFIISNAT YKEIGLLTCE ATVNGHLYKT NYLTHPQTNT IIDVVLSPSH GIELSVGEKL

       130        140        150        160        170        180
VLNCTARTEL NVGIDFNWEY PSSKHQHKKL VNRDLKTQSG SEMKKFLSTL TIDGVTRSDQ

       190        200        210        220        230        240
GLYTCAASSG LMTKKNSTFV RVHEKDKTHT CPPCPAPELL GGPSVFLFPP KPKDTLMISR

       250        260        270        280        290        300
TPEVTCVVVD VSHEDPEVKF NWYVDGVEVH NAKTKPREEQ YNSTYRVVSV LTVLHQDWLN

       310        320        330        340        350        360
GKEYKCKVSN KALPAPIEKT ISKAKGQPRE PQVYTLPPSR DELTKNQVSL TCLVKGFYPS

       370        380        390        400        410        420
DIAVEWESNG QPENNYKTTP PVLDSDGSFF LYSKLTVDKS PWQQGNVFSC SVMHEALHNH

       430        440        450        460        470        480
YTQKSLSLSP GKGGGGGAQQ EECEWDPWTC EHMGSGSATG GSGSTASSGS GSATHQEECE

       490
WDPWTCEHML E
```

SEQ ID NO: 7, L1-7
AQQTNFMPM DDLEQRLYEQ FILQQG

SEQ ID NO: 8, L1-10
AQQKFQPLD ELEQTLYEQF MLQQA

SEQ ID NO: 9, L1-15
AQQKYQPLD ELDKTLYDQF MLQQG

SEC) ID NO: 10, L1-7B
QTNFMPM DDLEQRLYEQ FILQQG

SEQ ID NO: 11, L1-10B
QKFQPLD ELEQTLYEQF MLQQA

-continued

| SEQUENCES |
|---|

SEQ ID NO: 12, L1-15B
QKYQPLD ELDKTLYDQF MLQQG

SEQ ID NO: 13, Linker
(GGGGS)n
wherein n = 0-4

SEQ ID NO: 14, L1-15/Light Chain Fusion molecule
AQQKYQPLDELDKTLYDQFMLQQGGGGGSGGGGSGGGGSDIQMTQSPSSLSASVGDRVTITCSASQDISNYLNWYQQ
KPGKAPKVLIYFTSSLHSGVPSRFSGSGSGTDFTLTISSLQPEDFATYYCQQYSTVPWTFGQGTKVEIKRTVAAPSV
FIFPPSDEQLKSGTASVVCLLNNFYPREAKVQWKVDNALQSGNSQESVTEQDSKDSTYSLSSTLTLSKADYEKHKVY
ACEVTHQGLSSPVTKSFNRGEC SEQ ID NO: 15, L1-15 Heavy Chain Fusion Molecule
AQQKYQPLDELDKTLYDQFMLQQGGGGGSGGGGSGGGGSEVQLVESGGGLVQPGGSLRLSCAASGYTFTNYGMNWVR
QAPGKGLEWVGWINTYTGEPTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYSKLTVDKSRW
QQGNVFSCSVMHEALHNHYTQKSLSLSPGK SEQ ID NO: 16, L1-15 with LE Heavy Chain Fusion Molecule
AQQKYQPLDELDKTLYDQFMLQQLEGGGGGSGGGGSGGGGSEQQLVESGGGLVQPGGSLRLSCAASGYTFTNYGMNW
VRQAPGKGLEWVGWINTYTGEPTYAADFKRRFTFSLDTSKSTAYLQMNSLRAEDTAVYYCAKYPHYYGSSHWYFDVW
GQGTLVTVSSASTKGPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSPGK SEQ ID NO: 17, 2xCon4(C) fused to the C-terminus of the Heavy Chain of Bevacizumab, with linker peptide GGGGSGGGGSGGGGS 10 20 30 40 50 60
EVQLVESGGG LVQPGGSLPL SCAASGYTFT NYGMNWVRQA PGKGLEWVGW INTYTGEPTY 70 80 90 100 110 120
AADFKRRFTF SLDTSKSTAY LQMNSLRAED TAVYYCAKYP HYYGSSHWYF DVWGQGTLVT 130 140 150 160 170 180
VSSASTKGPS VFPLAPSSKS TSGGTAALGC LVKDYFPEPV TVSWNSGALT SGVHYFPAVL 190 200 210 220 230 240
QSSGLYSLSS VVTVPSSSLG TQTYICNVNH KPSNTKVDKK VEPKSCDKTH TCPPCPAPEL 250 260 270 280 290 300
LGGPSVFLFP PKPKDTLMIS RTPEVTCVVV DVSHEDPEVK FNWYVDGVEV HNAKTKPREE 310 320 330 340 350 360
QYNSTYRVVS VLTVLHQDWL NGKEYKCKVS NKALPAPIEK TISKAKGQPR EPQVYTLPPS 370 380 390 400 410 420
REEMTKNQVS LTCLVKGFYP SDIAVEWESN GQPENNYKTT PPVLDSDGSF FLYSKLTVDK 430 440 450 460 470 480
SPWQQGNVFS CSVMHEALHN HYTQKSLSLS PGKGGGGGAQ QEECEWDPWT CEHMGGGGSG 490 500
GGGSGGGGSA THQEECEWDPW TCEHMLE SEQ ID NO: 18, L1-15 fused to the N-terminus of the VEGF Trap, with linker peptide GGGGSGGGGSGGGGS 10 20 30 40 50 60
AQQKYQPLDE LDKTLYDQFM LQQGGGGGSG GGGSGGGGSS DTGRPFVEMY SEIPEIIHMT 70 80 90 100 110 120
EGRELVIPCR VTSPNITVTL KKFPLDTLIP DGKRIIWDSR KGFIISNATY KEIGLLTCEA 130 140 150 160 170 180
TVNGHLYKTN YLTHRQTNTI IDVVLSPSHG IELSVGEKLV LNCTARTELN VGIDFNWEYP 190 200 210 220 230 240
SSKHQHKKLV NRDLKTQSGS EMKKFLSTLT IDGVTRSDQG LYTCAASSGL MTKKNSTFVR 250 260 270 280 290 300
VHEKDKTHTC PPCPAPELLS GPSVFLFPPK PKDTLMISRT PEVTCVVVDV SHEDPEVKFN -continued

SEQUENCES

```
      310        320        330        340        350        360
WYVDGVEVHN AKTKPREEQY NSTYRVVSVL TVLHQDWLNG KEYKCKVSNK ALPAPIEKTI

      370        380        390        400        410        420
SKAKGQPREP QVYTLPPSRD ELTKNQVSLT CLVKGFYPSD LAVEWESNGQ PENNYKTTPP

      430        440        450        460        470
VLDSDGSFFL YSKLTVDKSR WQQGNVFSCS VMHEALHNHY TQKSLSLSPG K
```

SEQ ID NO: 19, DNA sequence (DHAMDH02083016) for 2xCon4(C) fused to the C-terminus of the Heavy Chain of Bevacizumab, with linker peptide GGGGSGGGGSGGGGS

```
ATGGGTTGGTCCTGTATCATTCTTTTCCTCGTCGCCACTGCCACCGGAGTCCACTCAGAAGTCCAGTTGGTGGAGTC
GGGAGGAGGACTGGTGCAGCCAGGCGGCTCCCTGCGCCTGTCCTGCGCGGCGTCCGGGTACACCTTCACCAACTACG
GCATGAACTGGGTCCGCCAGGCCCCCGGAAAGGGGCTGGAATGGGTCGGCTGGATCAACACTTACACCGGAGAACCT
ACCTACGCTGCCGATTTCAAGCGGCGCTTTACTTTCTCGCTGGACACCTCCAAGAGCACCGCCTATCTCCAAATGAA
CTCCCTGCGGGCCGAGGATACCGCCGTGTACTATTGCGCGAAGTACCCCCACTATTACGGTTCGTCCCATTGGTACT
TCGACGTCTGGGGCCAGGGAACTCTTGTCACTGTGTCCTCCGCATCCACCAAGGGACCGTCAGTGTTCCCCCTGGCC
CCGTCCTCCAAAAGCACTAGCGGAGGAACCGCAGCCTTGGGATGCCTCGTCAAGGACTACTTTCCCGAGCCTGTCAC
CGTGTCGTGGAACTCCGGTGCCCTCACTTCGGGCGTGCACACGTTCCCAGCGGTGCTGCAGTCCAGCGGACTGTACT
CGCTGTCCTCCGTCGTGACCGTGCCTTCATCGAGCCTGGGGACCCAGACCTACATTTGCAACGTGAACCACAAGCCC
TCCAACACCAAAGTGGACAAGAAGGTCGAACCAAAGAGCTGCGACAAGACCCACACTTGCCCGCCGTGCCCGGCCCC
TGAGTTGCTGGGTGGTCCATCGGTGTTCCTGTTCCCGCCTAAGCCGAAGGACACACTCATGATCAGCAGGACCCCCG
AAGTGACCTGTGTGGTGGTCGACGTGTCACATGAAGATCCCGAGGTCAAGTTCAATTGGTACGTGGACGGAGTGGAA
GTGCATAATGCCAAGACTAAGCCGAGAGAGGAACAGTACAACTCCACCTACCGGGTGGTGTCAGTGCTGACCGTGCT
CCATCAGGACTGGCTCAACGGGAAGGAGTACAAGTGCAAAGTGTCGAACAAGGCTCTCCCCGCCCCTATCGAGAAAA
CCATTAGCAAGGCTAAGGGACAGCCGCGGGAGCCGCAAGTGTACACCCTGCCCCCGAGCCGCGAAGAAATGACTAAG
AACCAAGTGTCCCTGACCTGTCTCGTGAAAGGGTTCTACCCGTCGGACATCGCTGTGGAGTGGGAGTCTAATGGTCA
ACCTGAGAACAACTACAAGACTACTCCCCCTGTGCTGGACTCCGATGGTTCCTTTTTCCTGTACTCAAAGCTGACCG
TGGACAAGTCCAGATGGCAGCAGGGCAACGTGTTCAGCTGCTCCGTGATGCATGAAGCACTTCACAACCACTACACC
CAGAAGTCCCTCAGCCTGTCTCCGGGGAAGGGCGGCGGAGGAGGGGCCCAGCAGGAAGAGTGTGAATGGGACCCCTG
GACTTGTGAACACATGGGCGGCGGCGGCTCCGGTGGAGGAGGATCCGGCGGAGGGGGCAGCGCGACGCACCAGGAGG
AGTGCGAATGGGATCCATGGACTTGCGAACACATGCTGGAGTGA
```

SEQ ID NO: 20, DNA sequence (DHAMDL083016), for the light chain of Bevacizumab

```
ATGGGTTGGTCCTGTATTATCCTCTTTCTCGTCGCCACTGCCACCGGAGTGCACTCAGATATTCAGATGACCCAGAG
CCCCTCCTCACTGTCCGCTTCCGTGGGGGACCGCGTGACTATCACTTGCTCGGCTTCCCAAGATATCTCCAACTACC
TGAACTGGTACCAGCAGAAGCCCGGAAAGGCCCCGAAAGTGCTCATCTACTTCACCTCATCGCTGCACTCGGGAGTG
CCCTCAAGATTTTCCGGCTCCGGAAGCGGGACCGACTTCACTCTTACCATCTCATCGTTGCAACCAGAGGATTTCGC
GACCTACTACTGTCAGCAGTACTCCACGGTGCCGTGGACCTTCGGACAAGGCACCAAAGTGGAGATCAAGAGGACTG
TGGCGGCCCCGAGCGTGTTCATTTTCCCTCCTTCCGACGAGCAGCTGAAAAGCGGCACCGCCTCGGTCGTGTGCCTC
CTGAACAACTTCTACCCGCGGGAAGCCAAGGTCCAGTGGAAGGTCGACAACGCGCTGCAGAGCGGAAATTCCCAGGA
GAGCGTGACCGAACAGGACTCCAAGGACAGCACCTATTCCCTGTCGTCTACACTGACCCTGAGCAAGGCCGACTACG
AGAAGCATAAGGTCTACGCATGCGAAGTGACCCACCAAGGTCTTTCCTCCCCTGTGACCAAGTCCTTCAACCGGGGC
GAATGCTGA
```

SEQ ID NO: 21, DNA sequence (LY2.55.1), for peptide L1-15 (no LE) fused to the N-terminus of the light chain of Bevacizumab

```
ATGGCCTGGATGATGTTGCTTCTCGGACTTCTCGCGTATGGATCAGGGGTGGATAGCGCGCAACAGAAGTACCAGCC
TTTGGACGAACTGGACAAGACCCTGTACGACCAGTTCATGCTGCAACAGGGAGGGGGCGGTGGATCCGGGGGCGGCG
GCTCCGGCGGTGGCGGATCCGACATTCAAATGACTCAGTCGCCATCGTCCCTCTCGGCATCCGTGGGAGACAGAGTG
ACCATCACTTGTTCCGCCTCGCAAGACATCTCCAACTACCTGAACTGGTACCAGCAGAAGCCCGGGAAGGCCCCCAA
AGTGCTCATCTACTTTACTTCCTCACTGCACTCCGGGGTGCCAAGCCGCTTTAGCGGCTCCGGTTCTGGAACCGATT
TCACCCTGACCATTAGCTCACTCCAGCCGGAAGATTTCGCTACGTACTACTGCCAGCAGTATTCGACCGTGCCGTGG
ACTTTCGGACAGGGTACCAAAGTCGAGATCAAGCGGACCGTGGCCGCCCCGAGCGTGTTCATTTTCCCGCCTTCCGA
CGAGCAACTCAAGTCCGGCACTGCCTCCGTGGTCTGCCTGCTGAACAATTTCTACCCCCGCGAGGCTAAGGTCCAGT
GGAAGGTCGATAACGCACTGCAGTCCGGAAACAGCCAAGAGAGCGTGACCGAACAGGACTCCAAGGACTCAACTTAC
TCGCTGAGCTCCACCCTGACCCTGTCGAAGGCCGACTACGAAAAGCACAAAGTGTACGCCTGCGAAGTGACACATCA
GGGCCTGTCATCCCCTGTCACCAAGTCCTTCAACCGGGGAGAGTGCTGATAA
```

SEQ ID NO: 22, DNA sequence (LY2.55.2), for peptide L1-15 (with LE) fused to the N-terminus of the light chain of Bevacizumab

```
ATGGCCTGGATGATGTTGCTTCTCGGACTTCTCGCGTATGGATCAGGGGTGGATAGCGCGCAACAGAAGTACCAGCC
TTTGGACGAACTGGACAAGACCCTGTACGACCAGTTCATGCTGCAACAGGGACTGGAAGGGGGCGGTGGATCCGGGG
GCGGCGGCTCCGGCGGTGGCGGATCCGACATTCAAATGACTCAGTCGCCATCGTCCCTCTCGGCATCCGTGGGAGAC
AGAGTGACCATCACTTGTTCCGCCTCGCAAGACATCTCCAACTACCTGAACTGGTACCAGCAGAAGCCCGGGAAGGC
CCCCAAAGTGCTCATCTACTTTACTTCCTCACTGCACTCCGGGGTGCCAAGCCGCTTTAGCGGCTCCGGTTCTGGAA
CCGATTTCACCCTGACCATTAGCTCACTCCAGCCGGAAGATTTCGCTACGTACTACTGCCAGCAGTATTCGACCGTG
CCGTGGACTTTCGGACAGGGTACCAAAGTCGAGATCAAGCGGACCGTGGCCGCCCCGAGCGTGTTCATTTTCCCGCC
TTCCGACGAGCAACTCAAGTCCGGCACTGCCTCCGTGGTCTGCCTGCTGAACAATTTCTACCCCCGCGAGGCTAAGG
TCCAGTGGAAGGTCGATAACGCACTGCAGTCCGGAAACAGCCAAGAGAGCGTGACCGAACAGGACTCCAAGGACTCA
ACTTACTCGCTGAGCTCCACCCTGACCCTGTCGAAGGCCGACTACGAAAAGCACAAAGTGTACGCCTGCGAAGTGAC
ACATCAGGGCCTGTCATCCCCTGTCACCAAGTCCTTCAACCGGGGAGAGTGCTGATAA
```

-continued

SEQUENCES

SEQ ID NO: 23, DNA sequence (LY2.55.3), for peptide L1-15 (no LE) fused to the N-terminus of the heavy chain of Bevacizumab

```
ATGGCTTGGATGATGCTGCTGCTTGGCCTTCTCGCATACGGTTCCGGAGTCGATAGCGCCCAACAGAAGTACCAGCC
TCTGGACGAACTGGATAAGACCCTGTACGATCAGTTCATGCTGCAACAGGGGGGCGGCGGAGGATCGGGCGGTGGTG
GATCCGGCGGCGGCGGATCCGAAGTGCAGCTCGTGGAGAGCGGGGGCGGACTCGTGCAGCCGGGAGGTTCGCTGAGA
TTGTCCTGTGCCGCCTCCGGTTACACCTTTACCAATTACGGGATGAACTGGGTCCGCCAGGCCCCCGGAAAGGGACT
GGAATGGGTCGGCTGGATCAACACATATACCGGAGAGCCCACCTACGCCGCGGACTTCAAGCGGAGATTCACCTTTT
CACTGGATACGTCAAAGTCAACTGCATACCTCCAGATGAACTCCCTTAGGGCGGAAGATACCGCCGTGTACTACTGC
GCCAAGTACCCGCACTATTACGGGTCCAGCCATTGGTACTTCGACGTCTGGGGACAGGGGACCCTCGTGACCGTCAG
CAGCGCCTCCACCAAGGGCCCGTCCGTGTTCCCTCTTGCGCCGTCGTCCAAAAGCACTTCCGGCGGCACTGCCGCCC
TGGGCTGCCTCGTGAAGGATTACTTCCCGGAACCGGTCACCGTGTCGTGGAACTCCGGAGCCCTGACTTCGGGTGTC
CACACCTTCCCTGCGGTGCTGCAGAGCTCCGGTCTGTACTCCCTCTCTTCCGTGGTCACGGTGCCCTCCTCATCACT
GGGAACCCAGACCTACATCTGCAACGTGAACCACAAGCCCTCAAACACTAAGGTCGACAAGAAAGTCGAACCGAAGT
CGTGCGACAAGACCCACACTTGCCCTCCGTGCCCGGCTCCCGAGCTGCTGGGGGGCCCTTCCGTGTTTTTGTTCCCG
CCGAAACCAAAGGACACTCTGATGATCAGCCGCACTCCGGAAGTGACCTGTGTGGTGGTGGACGTGTCCCACGAGGA
CCCAGAAGTGAAATTCAATTGGTACGTGGATGGCGTGGAAGTGCACAACGCTAAGACTAAGCCCCGCGAGGAACAGT
ACAACAGCACTTACCGGGTGGTGTCGGTGCTCACCGTGCTGCACCAAGATTGGCTCAACGGGAAGGAGTACAAGTGC
AAAGTCTCCAACAAGGCCCTGCCCGCACCTATTGAAAAGACCATCAGCAAGGCCAAGGGACAGCCCCGGGAGCCCCA
GGTCTACACCCTGCCTCCCTCGCGCGAAGAGATGACTAAGAACCAAGTGTCCCTGACCTGTCTGGTCAAGGGATTCT
ATCCTTCCGACATTGCCGTGGAATGGGAGTCCAACGGGCAGCCAGAGAACAACTACAAGACCACTCCACCTGTGCTG
GACTCCGACGGGTCCTTCTTCTTGTACTCGAAGCTGACCGTGGACAAGTCCCGGTGGCAGCAGGGAAACGTGTTCAG
CTGCTCCGTGATGCACGAGGCCTTGCATAATCATTACACCCAAAAGTCGCTGAGCTTGAGCCCGGGAAAGTGATAA
```

SEQ ID NO: 24, DNA sequence (LY2.55.4), for peptide L1-15 (with LE) fused to the N-terminus of the heavy chain of Bevacizumab

```
ATGGCTTGGATGATGCTGCTGCTTGGCCTTCTCGCATACGGTTCCGGAGTCGATAGCGCCCAACAGAAGTACCAGCC
TCTGGACGAACTGGATAAGACCCTGTACGATCAGTTCATGCTGCAACAGGGGCTTGAGGGCGGCGGAGGATCGGGCG
GTGGTGGATCCGGCGGCGGCGGATCCGAAGTGCAGCTCGTGGAGAGCGGGGGCGGACTCGTGCAGCCGGGAGGTTCG
CTGAGATTGTCCTGTGCCGCCTCCGGTTACACCTTTACCAATTACGGGATGAACTGGGTCCGCCAGGCCCCCGGAAA
GGGACTGGAATGGGTCGGCTGGATCAACACATATACCGGAGAGCCCACCTACGCCGCGGACTTCAAGCGGAGATTCA
CCTTTTCACTGGATACGTCAAAGTCAACTGCATACCTCCAGATGAACTCCCTTAGGGCGGAAGATACCGCCGTGTAC
TACTGCGCCAAGTACCCGCACTATTACGGGTCCAGCCATTGGTACTTCGACGTCTGGGGACAGGGGACCCTCGTGAC
CGTCAGCAGCGCCTCCACCAAGGGCCCGTCCGTGTTCCCTCTTGCGCCGTCGTCCAAAAGCACTTCCGGCGGCACTG
CCGCCCTGGGCTGCCTCGTGAAGGATTACTTCCCGGAACCGGTCACCGTGTCGTGGAACTCCGGAGCCCTGACTTCG
GGTGTCCACACCTTCCCTGCGGTGCTGCAGAGCTCCGGTCTGTACTCCCTCTCTTCCGTGGTCACGGTGCCCTCCTC
ATCACTGGGAACCCAGACCTACATCTGCAACGTGAACCACAAGCCCTCAAACACTAAGGTCGACAAGAAAGTCGAAC
CGAAGTCGTGCGACAAGACCCACACTTGCCCTCCGTGCCCGGCTCCCGAGCTGCTGGGGGGCCCTTCCGTGTTTTTG
TTCCCGCCGAAACCAAAGGACACTCTGATGATCAGCCGCACTCCGGAAGTGACCTGTGTGGTGGTGGACGTGTCCCA
CGAGGACCCAGAAGTGAAATTCAATTGGTACGTGGATGGCGTGGAAGTGCACAACGCTAAGACTAAGCCCCGCGAGG
AACAGTACAACAGCACTTACCGGGTGGTGTCGGTGCTCACCGTGCTGCACCAAGATTGGCTCAACGGGAAGGAGTAC
AAGTGCAAAGTCTCCAACAAGGCCCTGCCCGCACCTATTGAAAAGACCATCAGCAAGGCCAAGGGACAGCCCCGGGA
GCCCCAGGTCTACACCCTGCCTCCCTCGCGCGAAGAGATGACTAAGAACCAAGTGTCCCTGACCTGTCTGGTCAAGG
GATTCTATCCTTCCGACATTGCCGTGGAATGGGAGTCCAACGGGCAGCCAGAGAACAACTACAAGACCACTCCACCT
GTGCTGGACTCCGACGGGTCCTTCTTCTTGTACTCGAAGCTGACCGTGGACAAGTCCCGGTGGCAGCAGGGAAACGT
GTTCAGCTGCTCCGTGATGCACGAGGCCTTGCATAATCATTACACCCAAAAGTCGCTGAGCTTGAGCCCGGGAAAGT
GATAA
```

SEQ ID NO: 25, DNA sequence (LY2.55.5), for the light chain of Bevacizumab

```
ATGGCCTGGATGATGTTGCTTCTCGGACTTCTCGCGTATGGATCAGGGGTGGACTCCGACATTCAAATGACTCAGTC
GCCATCGTCCCTCTCGGCATCCGTGGGAGACAGAGTGACCATCACTTGTTCCGCCTCGCAAGACATCTCCAACTACC
TGAACTGGTACCAGCAGAAGCCCGGGAAGGCCCCCAAAGTGCTCATCTACTTTACTTCCTCACTGCACTCCGGGGTG
CCAAGCCGCTTTAGCGGCTCCGGTTCTGGAACCGATTTCACCCTGACCATTAGCTCACTCCAGCCGGAAGATTTCGC
TACGTACTACTGCCAGCAGTATTCGACCGTGCCGTGGACTTTCGGACAGGGTACCAAAGTCGAGATCAAGCGGACCG
TGGCCGCCCCGAGCGTGTTCATTTTCCCGCCTTCCGACGAGCAACTCAAGTCCGGCACTGCCTCCGTGGTCTGCCTG
CTGAACAATTTCTACCCCCGCGAGGCTAAGGTCCAGTGGAAGGTCGATAACGCACTGCAGTCCGGAAACAGCCAAGA
GAGCGTGACCGAACAGGACTCCAAGGACTCAACTTACTCGCTGAGCTCCACCCTGACCCTGTCGAAGGCCGACTACG
AAAAGCACAAAGTGTACGCCTGCGAAGTGACACATCAGGGCCTGTCATCCCCTGTCACCAAGTCCTTCAACCGGGGA
GAGTGCTGATAA
```

SEQUENCE LISTING

```
Sequence total quantity: 25
SEQ ID NO: 1           moltype = AA  length = 59
FEATURE                Location/Qualifiers
REGION                 1..59
                       note = Peptide Fragment of Angiopoietin-2
source                 1..59
                       mol_type = protein
                       organism = synthetic construct
SEQUENCE: 1
GGGGGAQQEE CEWDPWTCEH MGSGSATGGS GSTASSGSGS ATHQEECEWD PWTCEHMLE   59
```

```
SEQ ID NO: 2            moltype = AA  length = 453
FEATURE                 Location/Qualifiers
REGION                  1..453
                        note = Heavy Chain of Bevacizumab
source                  1..453
                        mol_type = protein
                        organism = synthetic construct
SEQUENCE: 2
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                             453

SEQ ID NO: 3            moltype = AA  length = 214
FEATURE                 Location/Qualifiers
REGION                  1..214
                        note = Light Chain of Bevacizumab
source                  1..214
                        mol_type = protein
                        organism = synthetic construct
SEQUENCE: 3
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 4            moltype = AA  length = 512
FEATURE                 Location/Qualifiers
REGION                  1..512
                        note = Fusion protein of 2xCon4(C) fused to the C-terminus
                         of the Bevacizumab heavy chain
source                  1..512
                        mol_type = protein
                        organism = synthetic construct
SEQUENCE: 4
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGGAQ QEECEWDPWT CEHMGSGSAT  480
GGSGSTASSG SGSATHQEEC EWDPWTCEHM LE                              512

SEQ ID NO: 5            moltype = AA  length = 431
FEATURE                 Location/Qualifiers
REGION                  1..431
                        note = VEGF Trap Aflibercept
VARIANT                 431
                        note = X is G or K
source                  1..431
                        mol_type = protein
                        organism = synthetic construct
SEQUENCE: 5
SDTGRPFVEM YSEIPEIIHM TEGRELVIPC RVTSPNITVT LKKFPLDTLI PDGKRIIWDS  60
RKGFIISNAT YKEIGLLTCE ATVNGHLYKT NYLTHRQTNT IIDVVLSPSH GIELSVGEKL  120
VLNCTARTEL NVGIDFNWEY PSSKHQHKKL VNRDLKTQSG SEMKKFLSTL TIDGVTRSDQ  180
GLYTCAASSG LMTKKNSTFV RVHEKDKTHT CPPCPAPELL GGPSVFLFPP KPKDTLMISR  240
TPEVTCVVVD VSHEDPEVKF NWYVDGVEVH NAKTKPREEQ YNSTYRVVSV LTVLHQDWLN  300
GKEYKCKVSN KALPAPIEKT ISKAKGQPRE PQVYTLPPSR DELTKNQVSL TCLVKGFYPS  360
DIAVEWESNG QPENNYKTTP PVLDSDGSFF LYSKLTVDKS RWQQGNVFSC SVMHEALHNH  420
YTQKSLSLSP X                                                     431

SEQ ID NO: 6            moltype = AA  length = 491
FEATURE                 Location/Qualifiers
REGION                  1..491
                        note = Fusion protein of 2xCon4(C) fused to the C-terminus
                         of the VEGF Trap
source                  1..491
                        mol_type = protein
                        organism = synthetic construct
SEQUENCE: 6
SDTGRPFVEM YSEIPEIIHM TEGRELVIPC RVTSPNITVT LKKFPLDTLI PDGKRIIWDS  60
RKGFIISNAT YKEIGLLTCE ATVNGHLYKT NYLTHRQTNT IIDVVLSPSH GIELSVGEKL  120
```

```
VLNCTARTEL NVGIDFNWEY PSSKHQHKKL VNRDLKTQSG SEMKKFLSTL TIDGVTRSDQ  180
GLYTCAASSG LMTKKNSTFV RVHEKDKTHT CPPCPAPELL GGPSVFLFPP KPKDTLMISR  240
TPEVTCVVVD VSHEDPEVKF NWYVDGVEVH NAKTKPREEQ YNSTYRVVSV LTVLHQDWLN  300
GKEYKCKVSN KALPAPIEKT ISKAKGQPRE PQVYTLPPSR DELTKNQVSL TCLVKGFYPS  360
DIAVEWESNG QPENNYKTTP PVLDSDGSFF LYSKLTVDKS RWQQGNVFSC SVMHEALHNH  420
YTQKSLSLSP GKGGGGGAQQ EECEWDPWTC EHMGSGSATG GSGSTASSGS GSATHQEECE  480
WDPWTCEHML E                                                      491

SEQ ID NO: 7            moltype = AA  length = 25
FEATURE                 Location/Qualifiers
REGION                  1..25
                        note = L1-7 Angiopoietin-2 binding peptide
source                  1..25
                        mol_type = protein
                        organism = synthetic construct
SEQUENCE: 7
AQQTNFMPMD DLEQRLYEQF ILQQG                                        25

SEQ ID NO: 8            moltype = AA  length = 24
FEATURE                 Location/Qualifiers
REGION                  1..24
                        note = L1-10 Angiopoietin-2 binding peptide
source                  1..24
                        mol_type = protein
                        organism = synthetic construct
SEQUENCE: 8
AQQKFQPLDE LEQTLYEQFM LQQA                                         24

SEQ ID NO: 9            moltype = AA  length = 24
FEATURE                 Location/Qualifiers
REGION                  1..24
                        note = L1-15 Angiopoietin-2 binding peptide
source                  1..24
                        mol_type = protein
                        organism = synthetic construct
SEQUENCE: 9
AQQKYQPLDE LDKTLYDQFM LQQG                                         24

SEQ ID NO: 10           moltype = AA  length = 23
FEATURE                 Location/Qualifiers
REGION                  1..23
                        note = L1-7B Angiopoietin-2 binding peptide
source                  1..23
                        mol_type = protein
                        organism = synthetic construct
SEQUENCE: 10
QTNFMPMDDL EQRLYEQFIL QQG                                          23

SEQ ID NO: 11           moltype = AA  length = 22
FEATURE                 Location/Qualifiers
REGION                  1..22
                        note = L1-10B Angiopoietin-2 binding peptide
source                  1..22
                        mol_type = protein
                        organism = synthetic construct
SEQUENCE: 11
QKFQPLDELE QTLYEQFMLQ QA                                           22

SEQ ID NO: 12           moltype = AA  length = 22
FEATURE                 Location/Qualifiers
REGION                  1..22
                        note = L1-15B Angiopoietin-2 binding peptide
source                  1..22
                        mol_type = protein
                        organism = synthetic construct
SEQUENCE: 12
QKYQPLDELD KTLYDQFMLQ QG                                           22

SEQ ID NO: 13           moltype = AA  length = 5
FEATURE                 Location/Qualifiers
REGION                  1..5
                        note = Linker Angiopoietin-2 binding peptide
source                  1..5
                        mol_type = protein
                        organism = synthetic construct
SEQUENCE: 13
GGGGS                                                              5

SEQ ID NO: 14           moltype = AA  length = 253
```

```
FEATURE                 Location/Qualifiers
REGION                  1..253
                        note = L1-15/Light Chain Fusion molecule
source                  1..253
                        mol_type = protein
                        organism = synthetic construct
SEQUENCE: 14
AQQKYQPLDE LDKTLYDQFM LQQGGGGGSG GGGSGGGGSD IQMTQSPSSL SASVGDRVTI  60
TCSASQDISN YLNWYQQKPG KAPKVLIYFT SSLHSGVPSR FSGSGSGTDF TLTISSLQPE  120
DFATYYCQQY STVPWTFGQG TKVEIKRTVA APSVFIFPPS DEQLKSGTAS VVCLLNNFYP  180
REAKVQWKVD NALQSGNSQE SVTEQDSKDS TYSLSSTLTL SKADYEKHKV YACEVTHQGL  240
SSPVTKSFNR GEC                                                    253

SEQ ID NO: 15           moltype = AA  length = 492
FEATURE                 Location/Qualifiers
REGION                  1..492
                        note = L1-15 Heavy Chain Fusion Molecule
source                  1..492
                        mol_type = protein
                        organism = synthetic construct
SEQUENCE: 15
AQQKYQPLDE LDKTLYDQFM LQQGGGGGSG GGGSGGGGSE VQLVESGGGL VQPGGSLRLS  60
CAASGYTFTN YGMNWVRQAP GKGLEWVGWI NTYTGEPTYA ADFKRRFTFS LDTSKSTAYL  120
QMNSLRAEDT AVYYCAKYPH YYGSSHWYFD VWGQGTLVTV SSASTKGPSV FPLAPSSKST  180
SGGTAALGCL VKDYFPEPVT VSWNSGALTS GVHTFPAVLQ SSGLYSLSSV VTVPSSSLGT  240
QTYICNVNHK PSNTKVDKKV EPKSCDKTHT CPPCPAPELL GGPSVFLFPP KPKDTLMISR  300
TPEVTCVVVD VSHEDPEVKF NWYVDGVEVH NAKTKPREEQ YNSTYRVVSV LTVLHQDWLN  360
GKEYKCKVSN KALPAPIEKT ISKAKGQPRE PQVYTLPPSR EEMTKNQVSL TCLVKGFYPS  420
DIAVEWESNG QPENNYKTTP PVLDSDGSFF LYSKLTVDKS RWQQGNVFSC SVMHEALHNH  480
YTQKSLSLSP GK                                                     492

SEQ ID NO: 16           moltype = AA  length = 494
FEATURE                 Location/Qualifiers
REGION                  1..494
                        note = L1-15 with LE Heavy Chain Fusion Molecule
source                  1..494
                        mol_type = protein
                        organism = synthetic construct
SEQUENCE: 16
AQQKYQPLDE LDKTLYDQFM LQQLEGGGGG SGGGGSGGGG SEVQLVESGG GLVQPGGSLR  60
LSCAASGYTF TNYGMNWVRQ APGKGLEWVG WINTYTGEPT YAADFKRRFT FSLDTSKSTA  120
YLQMNSLRAE DTAVYYCAKY PHYYGSSHWY FDVWGQGTLV TVSSASTKGP SVFPLAPSSK  180
STSGGTAALG CLVKDYFPEP VTVSWNSGAL TSGVHTFPAV LQSSGLYSLS SVVTVPSSSL  240
GTQTYICNVN HKPSNTKVDK KVEPKSCDKT HTCPPCPAPE LLGGPSVFLF PPKPKDTLMI  300
SRTPEVTCVV VDVSHEDPEV KFNWYVDGVE VHNAKTKPRE EQYNSTYRVV SVLTVLHQDW  360
LNGKEYKCKV SNKALPAPIE KTISKAKGQP REPQVYTLPP SREEMTKNQV SLTCLVKGFY  420
PSDIAVEWES NGQPENNYKT TPPVLDSDGS FFLYSKLTVD KSRWQQGNVF SCSVMHEALH  480
NHYTQKSLSL SPGK                                                   494

SEQ ID NO: 17           moltype = AA  length = 508
FEATURE                 Location/Qualifiers
REGION                  1..508
                        note = Fusion protein of 2xCon4(C) fused to the C-terminus
                         of the Heavy Chain of Bevacizumab, with linker peptide
                         GGGGSGGGGSGGGGS
source                  1..508
                        mol_type = protein
                        organism = synthetic construct
SEQUENCE: 17
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGGAQ QEECEWDPWT CEHMGGGGSG  480
GGGSGGGGSA THQEECEWDP WTCEHMLE                                    508

SEQ ID NO: 18           moltype = AA  length = 471
FEATURE                 Location/Qualifiers
REGION                  1..471
                        note = L1-15 fused to the N-terminus of the VEGF Trap, with
                         linker peptide GGGGSGGGGSGGGGS
source                  1..471
                        mol_type = protein
                        organism = synthetic construct
SEQUENCE: 18
AQQKYQPLDE LDKTLYDQFM LQQGGGGGSG GGGSGGGGSS DTGRPFVEMY SEIPEIIHMT  60
```

-continued

```
EGRELVIPCR VTSPNITVTL KKFPLDTLIP DGKRIIWDSR KGFIISNATY KEIGLLTCEA  120
TVNGHLYKTN YLTHRQTNTI IDVVLSPSHG IELSVGEKLV LNCTARTELN VGIDFNWEYP  180
SSKHQHKKLV NRDLKTQSGS EMKKFLSTLT IDGVTRSDQG LYTCAASSGL MTKKNSTFVR  240
VHEKDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRD ELTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K           471

SEQ ID NO: 19          moltype = DNA  length = 1584
FEATURE                Location/Qualifiers
misc_feature           1..1584
                       note = DNA sequence (DHAMDH02083016) for 2xCon4(C) fused to
                        the C-terminus of the Heavy Chain of Bevacizumab, with
                        linker peptide GGGGSGGGGSGGGGS
source                 1..1584
                       mol_type = other DNA
                       organism = synthetic construct
SEQUENCE: 19
atgggttggt cctgtatcat tcttttcctc gtcgccactg ccaccggagt ccactcagaa  60
gtccagttgg tggagtcggg aggaggactg gtgcagccag gcggctccct gcgcctgtcc  120
tgcgcggcgt ccgggtacac cttcaccaac tacggcatga actgggtccg ccaggccccc  180
ggaaaggggc tggaatgggt cggctggatc aacacttaca ccggagaacc tacctacgct  240
gccgatttca agcggcgctt tactttctcg ctggacacct ccaagagcac cgcctatctc  300
caaatgaact ccctgcgggc cgaggatacc gccgtgtact attgcgcgaa gtacccccac  360
tattacggtt cgtcccattg gtacttcgac gtctggggcc agggaactct tgtcactgtg  420
tcctccgcat ccaccaaggg accgtcagtg ttcccccctgg ccccgtcctc caaaagcact  480
agcggaggaa ccgcagcctt gggatgcctc gtcaaggact actttcccga gcctgtcacc  540
gtgtcgtgga actccggtgc cctcacttcg ggcgtgcaca cgttcccagc ggtgctgcag  600
tccagcggac tgtactcgct gtcctccgtc gtgaccgtgc cttcatcgag cctggggacc  660
cagacctaca tttgcaacgt gaaccacaag ccctccaaca ccaaagtgga caagaaggtc  720
gaaccaaaga gctgcgacaa gacccacact tgcccgccgt gcccggcccc tgagttgctg  780
ggtggtccat cggtgttcct gttcccgcct aagccgaagg acacactcat gatcagcagg  840
acccccgaag tgacctgtgt ggtggtcgac gtgtcacatg aagatcccga ggtcaagttc  900
aattggtacg tggacggagt ggaagtgcat aatgccaaga ctaagccgag agaggaacag  960
tacaactcca cctaccgggt ggtgtcagtg ctgaccgtgc tccatcagga ctggctcaac  1020
gggaaggagt acaagtgcaa agtgtcgaac aaggctctcc ccgcccctat cgagaaaacc  1080
attagcaagg ctaagggaca gccgcgggag ccgcaagtgt acaccctgcc cccgagccgc  1140
gaagaaatga ctaagaacca agtgtccctg acctgtctcg tgaaagggtt ctacccgtcg  1200
gacatcgctg tggagtggga gtctaatggt caacctgaga acaactacaa gactactccc  1260
cctgtgctgg actccgatgg ttcctttttc ctgtactcaa agctgaccgt ggacaagtcc  1320
agatggcagc agggcaacgt gttcagctgc tccgtgatgc atgaagcact tcacaaccac  1380
tacacccaga agtccctcag cctgtctccg ggaaagggcg gcggaggagg ggcccagcag  1440
gaagagtgtg aatgggaccc ctggacttgt gaacacatgg gcggcggcgg ctccggtgga  1500
ggaggatccg gcggaggggg cagcgcgacg caccaggagg agtgcgaatg ggatccatgg  1560
acttgcgaac acatgctgga gtga                                        1584

SEQ ID NO: 20          moltype = DNA  length = 702
FEATURE                Location/Qualifiers
misc_feature           1..702
                       note = DNA sequence (DHAMDL083016), for the light chain of
                        Bevacizumab
source                 1..702
                       mol_type = other DNA
                       organism = synthetic construct
SEQUENCE: 20
atgggttggt cctgtattat cctctttctc gtcgccactg ccaccggagt gcactcagat  60
attcagatga cccagagccc ctcctcactg tccgcttccg tgggggaccg cgtgactatc  120
acttgctcgg cttcccaaga tatctccaac tacctgaact ggtaccagca gaagcccgga  180
aaggccccga aagtgctcat ctacttcacc tcatcgctgc actcgggagt gccctcaaga  240
ttttccggct ccggaagcgg gaccgacttc actcttacca tctcatcgtt gcaaccagag  300
gatttcgcga cctactactg tcagcagtac tccacggtgc cgtggacctt cggacaaggc  360
accaaagtgg agatcaagag gactgtggcg gccccgagcg tgttcatttt ccctccttcc  420
gacgagcagc tgaaaagcgg caccgcctcg gtcgtgtgcc tcctgaacaa cttctacccg  480
cgggaagcca aggtccagtg gaaggtcgac aacgcgctgc agagcggaaa ttcccaggag  540
agcgtgaccg aacaggactc caaggacagc acctattccc tgtcgtctac actgaccctg  600
agcaaggccg actacgagaa gcataaggtc tacgcatgcg aagtgaccca ccaaggtctt  660
tcctccccctg tgaccaagtc cttcaaccgg ggcgaatgct ga                    702

SEQ ID NO: 21          moltype = DNA  length = 822
FEATURE                Location/Qualifiers
misc_feature           1..822
                       note = , DNA sequence (LY2.55.1), for peptide L1-15 (no LE)
                        fused to the N-terminus of the light chain of Bevacizumab
source                 1..822
                       mol_type = other DNA
                       organism = synthetic construct
SEQUENCE: 21
atggcctgga tgatgttgct tctcggactt ctcgcgtatg gatcaggggt ggatagcgcg  60
caacagaagt accagccttt ggacgaactg gacaagaccc tgtacgacca gttcatgctg  120
```

```
caacagggag ggggcggtgg atccgggggc ggcggctccg gcggtggcgg atccgacatt  180
caaatgactc agtcgccatc gtccctctcg gcatccgtgg gagacagagt gaccatcact  240
tgttccgcct cgcaagacat ctccaactac ctgaactggt accagcagaa gcccgggaag  300
gcccccaaag tgctcatcta ctttacttcc tcactgcact ccggggtgcc aagccgcttt  360
agcggctccg gttctggaac cgatttcacc ctgaccatta gctcactcca gccggaagat  420
ttcgctacgt actactgcca gcagtattcg accgtgccgt ggactttcgg acagggtacc  480
aaagtcgaga tcaagcggac cgtggccgcc ccgagcgtgt tcattttccc gccttccgac  540
gagcaactca agtccggcac tgcctccgtg gtctgcctgc tgaacaattt ctacccccgc  600
gaggctaagg tccagtggaa ggtcgataac gcactgcagt ccggaaacag ccaagagagc  660
gtgaccgaac aggactccaa ggactcaact tactcgctga gctccaccct gaccctgtcg  720
aaggccgact acgaaaagca caaagtgtac gcctgcgaag tgacacatca gggcctgtca  780
tcccctgtca ccaagtcctt caaccgggga gagtgctgat aa                      822
```

```
SEQ ID NO: 22           moltype = DNA  length = 828
FEATURE                 Location/Qualifiers
misc_feature            1..828
                        note = DNA sequence (LY2.55.2), for peptide L1-15 (with LE)
                         fused to the N-terminus of the light chain of Bevacizumab
source                  1..828
                        mol_type = other DNA
                        organism = synthetic construct
SEQUENCE: 22
atggcctgga tgatgttgct tctcggactt ctcgcgtatg gatcaggggt ggatagcgcg  60
caacagaagt accagccttt ggacgaactg gacaagaccc tgtacgacca gttcatgctg  120
caacagggac tggaaggggg cggtggatcc gggggcggcg gctccggcgg tggcggatcc  180
gacattcaaa tgactcagtc gccatcgtcc ctctcggcat ccgtgggaga cagagtgacc  240
atcacttgtt ccgcctcgca agacatctcc aactacctga actggtacca gcagaagccc  300
gggaaggccc ccaaagtgct catctacttt acttcctcac tgcactccgg ggtgccaagc  360
cgctttagcg gctccggttc tggaaccgat ttcaccctga ccattagctc actccagccg  420
gaagatttcg ctacgtacta ctgccagcag tattcgaccg tgccgtggac tttcggacag  480
ggtaccaaag tcgagatcaa gcggaccgtg gccgccccga gcgtgttcat tttcccgcct  540
tccgacgagc aactcaagtc cggcactgcc tccgtggtct gcctgctgaa caatttctac  600
ccccgcgagg ctaaggtcca gtggaaggtc gataacgcac tgcagtccgg aaacagccaa  660
gagagcgtga ccgaacagga ctccaaggac tcaacttact cgctgagctc caccctgacc  720
ctgtcgaagg ccgactacga aaagcacaaa gtgtacgcct gcgaagtgac acatcagggc  780
ctgtcatccc ctgtcaccaa gtccttcaac cggggagagt gctgataa                828
```

```
SEQ ID NO: 23           moltype = DNA  length = 1539
FEATURE                 Location/Qualifiers
misc_feature            1..1539
                        note = DNA sequence (LY2.55.3), for peptide L1-15 (no LE)
                         fused to the N-terminus of the heavy chain of Bevacizumab
source                  1..1539
                        mol_type = other DNA
                        organism = synthetic construct
SEQUENCE: 23
atggcttgga tgatgctgct gcttggcctt ctcgcatacg gttccggagt cgatagcgcc  60
caacagaagt accagcctct ggacgaactg gataagaccc tgtacgatca gttcatgctg  120
caacaggggg gcggcggagg atcgggcggt ggtggatccg gcggcggcgg atccgaagtg  180
cagctcgtgg agagcggggg cggactcgtg cagccgggag gttcgctgag attgtcctgt  240
gccgcctccg gttacacctt taccaattac gggatgaact gggtccgcca ggcccccgga  300
aagggactgg aatgggtcgg ctggatcaac acatataccg gagagcccac ctacgccgcg  360
gacttcaagc ggagattcac cttttcactg gatacgtcaa agtcaactgc atacctccag  420
atgaactccc ttagggcgga agataccgcc gtgtactact gcgccaagta cccgcactat  480
tacgggtcca gccattggta cttcgacgtc tggggacagg ggaccctcgt gaccgtcagc  540
agcgcctcca ccaagggccc gtccgtgttc cctcttgcgc cgtcgtccaa aagcacttcc  600
ggcggcactg ccgccctggg ctgcctcgtg aaggattact tcccggaacc ggtcaccgtg  660
tcgtggaact ccggagccct gacttcgggt gtccacacct tccctgcggt gctgcagagc  720
tccggtctgt actccctctc ttccgtggtc acggtgccct cctcatcact gggaacccag  780
acctacatct gcaacgtgaa ccacaagccc tcaaacacta aggtcgacaa gaaagtcgaa  840
ccgaagtcgt gcgacaagac ccacacttgc cctccgtgcc cggctcccga gctgctgggg  900
ggcccttccg tgtttttgtt cccgccgaaa ccaaaggaca ctctgatgat cagccgcact  960
ccggaagtga cctgtgtggt ggtggacgtg tcccacgagg acccagaagt gaaattcaat  1020
tggtacgtgg atggcgtgga agtgcacaac gctaagacta agccccgcga ggaacagtac  1080
aacagcactt accgggtggt gtcggtgctc accgtgctgc accaagattg gctcaacggg  1140
aaggagtaca agtgcaaagt ctccaacaag gccctgcccg cacctattga aaagaccatc  1200
agcaaggcca agggacagcc ccgggagccc caggtctaca ccctgcctcc ctcgcgcgaa  1260
gagatgacta agaaccaagt gtccctgacc tgtctggtca agggattcta tccttccgac  1320
attgccgtgg aatgggagtc caacgggcag ccagagaaca actacaagac cactccacct  1380
gtgctggact ccgacgggtc cttcttcttg tactcgaagc tgaccgtgga caagtcccgg  1440
tggcagcagg gaaacgtgtt cagctgctcc gtgatgcacg aggccttgca taatcattac  1500
acccaaaagt cgctgagctt gagcccggga aagtgataa                          1539
```

```
SEQ ID NO: 24           moltype = DNA  length = 1545
FEATURE                 Location/Qualifiers
misc_feature            1..1545
                        note = DNA sequence (LY2.55.4), for peptide L1-15 (with LE)
                         fused to the N-terminus of the heavy chain of Bevacizumab
source                  1..1545
```

-continued

```
                         mol_type = other DNA
                         organism = synthetic construct
SEQUENCE: 24
atggcttgga tgatgctgct gcttggcctt ctcgcatacg gttccggagt cgatagcgcc  60
caacagaagt accagcctct ggacgaactg gataagaccc tgtacgatca gttcatgctg  120
caacaggggc ttgagggcgg cggaggatcg ggcggtggtg gatccggcgg cggcggatcc  180
gaagtgcagc tcgtggagag cgggggcgga ctcgtgcagc cgggaggttc gctgagattg  240
tcctgtgccg cctccggtta cacctttacc aattacggga tgaactgggt ccgccaggcc  300
cccggaaagg gactggaatg ggtcggctgg atcaacacat ataccggaga gcccacctac  360
gccgcggact tcaagcggag attcaccttt tcactggata cgtcaaagtc aactgcatac  420
ctccagatga actcccttag ggcggaagat accgccgtgt actactgcgc caagtacccg  480
cactattacg ggtccagcca ttggtacttc gacgtctggg gacaggggac cctcgtgacc  540
gtcagcagcg cctccaccaa gggcccgtcc gtgttccctc ttgcgccgtc gtccaaaagc  600
acttccggcg gcactgccgc cctgggctgc ctcgtgaagg attacttccc ggaaccggtc  660
accgtgtcgt ggaactccgg agccctgact tcgggtgtcc acaccttccc tgcggtgctg  720
cagagctccg gtctgtactc cctctcttcc gtggtcacgg tgccctcctc atcactggga  780
acccagacct acatctgcaa cgtgaaccac aagccctcaa acactaaggt cgacaagaaa  840
gtcgaaccga agtcgtgcga caagacccac acttgccctc cgtgcccggc tcccgagctg  900
ctggggggcc cttccgtgtt tttgttcccg ccgaaaccaa aggacactct gatgatcagc  960
cgcactccgg aagtgacctg tgtggtggtg gacgtgtccc acgaggaccc agaagtgaaa  1020
ttcaattggt acgtggatgg cgtggaagtg cacaacgcta agactaagcc ccgcgaggaa  1080
cagtacaaca gcacttaccg ggtggtgtcg gtgctcaccg tgctgcacca agattggctc  1140
aacgggaagg agtacaagtg caaagtctcc aacaaggccc tgcccgcacc tattgaaaag  1200
accatcagca aggccaaggg acagccccgg gagccccagg tctacaccct gcctccctcg  1260
cgcgaagaga tgactaagaa ccaagtgtcc ctgacctgtc tggtcaaggg attctatcct  1320
tccgacattg ccgtggaatg ggagtccaac gggcagccag agaacaacta caagaccact  1380
ccacctgtgc tggactccga cgggtccttc ttcttgtact cgaagctgac cgtggacaag  1440
tcccggtggc agcagggaaa cgtgttcagc tgctccgtga tgcacgaggc cttgcataat  1500
cattacaccc aaaagtcgct gagcttgagc ccgggaaagt gataa              1545

SEQ ID NO: 25            moltype = DNA  length = 705
FEATURE                  Location/Qualifiers
misc_feature             1..705
                         note = DNA sequence (LY2.55.5), for the light chain of
                          Bevacizumab
source                   1..705
                         mol_type = other DNA
                         organism = synthetic construct
SEQUENCE: 25
atggcctgga tgatgttgct tctcggactt ctcgcgtatg gatcaggggt ggactccgac  60
attcaaatga ctcagtcgcc atcgtccctc tcggcatccg tgggagacag agtgaccatc  120
acttgttccg cctcgcaaga catctccaac tacctgaact ggtaccagca gaagcccggg  180
aaggccccca aagtgctcat ctactttact tcctcactgc actccggggt gccaagccgc  240
tttagcggct ccggttctgg aaccgatttc accctgacca ttagctcact ccagccggaa  300
gatttcgcta cgtactactg ccagcagtat tcgaccgtgc cgtggacttt cggacagggt  360
accaaagtcg agatcaagcg gaccgtggcc gccccgagcg tgttcatttt cccgccttcc  420
gacgagcaac tcaagtccgg cactgcctcc gtggtctgcc tgctgaacaa tttctacccc  480
cgcgaggcta aggtccagtg gaaggtcgat aacgcactgc agtccggaaa cagccaagag  540
agcgtgaccg aacaggactc caaggactca acttactcgc tgagctccac cctgaccctg  600
tcgaaggccg actacgaaaa gcacaaagtg tacgcctgcg aagtgacaca tcagggcctg  660
tcatcccctg tcaccaagtc cttcaaccgg ggagagtgct gataa              705
```

The invention claimed is:

1. A chimeric molecule comprising the amino acid sequence of SEQ ID NO: 6.

2. A polynucleotide encoding the chimeric molecule of claim 1.

3. An expression vector comprising the polynucleotide of claim 2.

4. A host cell transfected with the vector of claim 3.

5. A method of producing a chimeric molecule comprising culturing the host cell of claim 4.

6. A pharmaceutical composition comprising the chimeric molecule of claim 1 and a pharmaceutically acceptable carrier.

* * * * *